United States Patent
Schultz

(10) Patent No.: US 12,208,226 B2
(45) Date of Patent: Jan. 28, 2025

(54) ABSCESS IRRIGATION SYSTEMS

(71) Applicant: Joseph P. Schultz, Atlanta, GA (US)

(72) Inventor: Joseph P. Schultz, Atlanta, GA (US)

( * ) Notice: Subject to any disclaimer, the term of this patent is extended or adjusted under 35 U.S.C. 154(b) by 587 days.

(21) Appl. No.: 17/365,014

(22) Filed: Jul. 1, 2021

(65) Prior Publication Data
US 2021/0322667 A1  Oct. 21, 2021

Related U.S. Application Data

(63) Continuation of application No. 16/596,347, filed on Oct. 8, 2019, now Pat. No. 11,083,835, which is a continuation of application No. 16/197,480, filed on Nov. 21, 2018, now Pat. No. 10,576,198, which is a continuation of application No. 14/296,651, filed on Jun. 5, 2014, now Pat. No. 10,363,356, which is a continuation of application No. 12/851,476, filed on Aug. 5, 2010, now Pat. No. 8,747,372.

(60) Provisional application No. 61/325,756, filed on Apr. 19, 2010, provisional application No. 61/231,638, filed on Aug. 5, 2009.

(51) Int. Cl.
*A61M 3/02* (2006.01)
*A61B 90/00* (2016.01)
*A61M 1/00* (2006.01)

(52) U.S. Cl.
CPC ........... *A61M 3/0279* (2013.01); *A61B 90/05* (2016.02); *A61M 1/77* (2021.05)

(58) Field of Classification Search
CPC ........ A61M 3/0279; A61M 1/77; A61B 90/05

USPC .................................................. 604/296, 289
See application file for complete search history.

(56) References Cited

U.S. PATENT DOCUMENTS

| | | |
|---|---|---|
| 3,648,696 A | 3/1972 | Keith |
| 3,991,762 A | 11/1976 | Radford |
| 4,643,197 A | 2/1987 | Greene et al. |
| D295,380 S | 4/1988 | Virag et al. |
| 4,769,003 A | 9/1988 | Stamler |
| 4,872,579 A | 10/1989 | Palmer |
| 4,898,588 A | 6/1990 | Roberts |
| 5,030,214 A | 7/1991 | Spector |
| 5,078,694 A | 1/1992 | Wallace |
| D344,133 S | 2/1994 | Stamler |
| D345,016 S | 3/1994 | Stamler |
| 5,368,017 A | 11/1994 | Sorenson et al. |
| 5,433,195 A | 7/1995 | Kee et al. |
| 5,562,077 A | 10/1996 | Schultz |
| 5,653,231 A | 8/1997 | Bell |
| 5,735,833 A | 4/1998 | Olson |
| 5,775,325 A | 7/1998 | Russo |
| 5,795,324 A | 8/1998 | Morse |

(Continued)

OTHER PUBLICATIONS

Judd Hollander, Wound Registry: Development and Validation, article, May 1995, Annals of Emergency Medicine.

(Continued)

*Primary Examiner* — Jacqueline F Stephens
(74) *Attorney, Agent, or Firm* — Merchant & Gould P.C.

(57) ABSTRACT

An irrigator system for delivering a volume of fluid from a fluid source to an abscess or wound. The irrigator system includes a fluid source connector for removably connecting to the fluid source, a fluid delivery nozzle for delivering the (Continued)

fluid to the abscess or wound, and a shield removably positioned around the fluid delivery nozzle to protect the fluid delivery nozzle.

20 Claims, 23 Drawing Sheets

(56) References Cited

U.S. PATENT DOCUMENTS

| | | | |
|---|---|---|---|
| 5,830,197 | A | 11/1998 | Rucinski |
| 5,941,859 | A | 8/1999 | Lerman |
| 6,082,361 | A | 7/2000 | Morejon |
| 6,093,182 | A | 7/2000 | Lampropoulis et al. |
| 6,210,381 | B1 | 4/2001 | Morse |
| 6,293,929 | B1 | 9/2001 | Smith et al. |
| 6,402,724 | B1 | 6/2002 | Smith et al. |
| 6,408,850 | B1 | 6/2002 | Sudge |
| 7,311,695 | B1 | 12/2007 | Schultz |
| 7,802,574 | B2 | 9/2010 | Schultz |
| 8,002,757 | B1 | 8/2011 | Schultz |
| 8,747,372 | B1 | 6/2014 | Schultz |
| 10,363,356 | B2 | 7/2019 | Schultz |
| 2001/0037095 | A1 | 11/2001 | Rucinski |
| 2002/0108614 | A1* | 8/2002 | Schultz ............ A61M 16/0486 128/207.14 |

OTHER PUBLICATIONS

Richard Edlich, Wound Irrigation, editorial, Jul. 1994, Annals of Emergency Medicine.
John Howell, Outpatient Wound Preparation and Care: A National Survey, article, Aug. 1992, Annals of Emergency Medicine.
Adam Singer, Pressure Dynamics of Various Irrigation Techniques Commonly Used in the Emergency Department, article, Jul. 1994, Annals of Emergency Medicine.
Judd Hollander, Irrigation of Facial and Scalp Lacerations: Does It Alter Outcome?, article, Jan. 1998, Annals of Emergency Medicine.
Thomas Stephenson, Cleansing the Traumatic Wound by High Pressure Syringe Irrigation, article, Jan. 1976, JACEP, vol. 5, No. 1.
Carey Chisolm, Comparison of a New Pressurized Saline Cannister Versus Syringe Irrigation for Laceration Cleansing in the Emergency Department, article, Nov. 1992, Annals of Emergency Medicine.
Richard Edlich, Principles of Emergency Room Management. article. Dec. 1988. Annals of Emergency Medicine.
Jeffrey Morse, Wound Infection Rate and Irrigation Pressure of Two Potential New Wound Irrigation Devices: The Port and the Cap. article. Jan. 1988, American Journal of Emergency Medicine, vol. 16, No. 1.

* cited by examiner

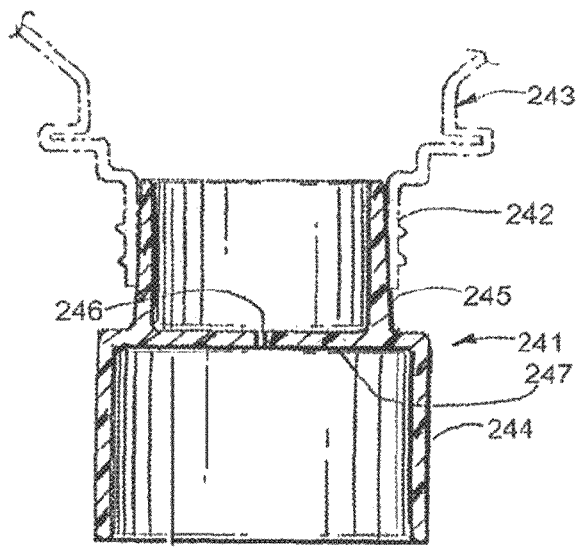
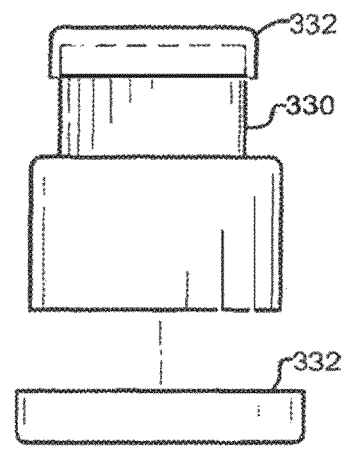
FIG. 17   FIG. 18
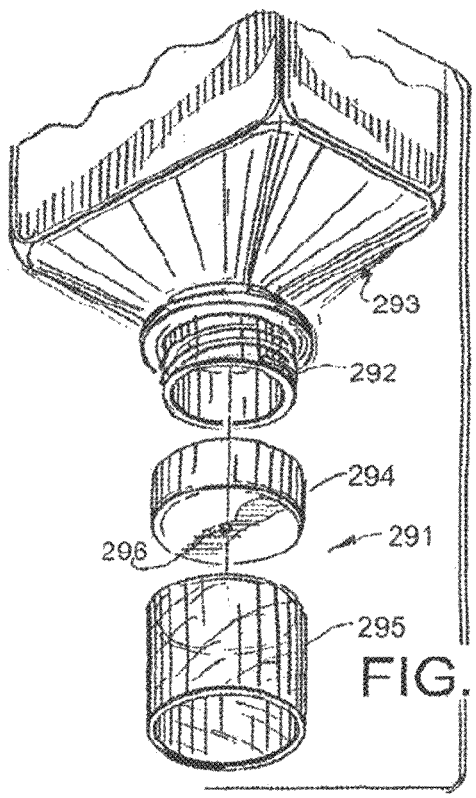
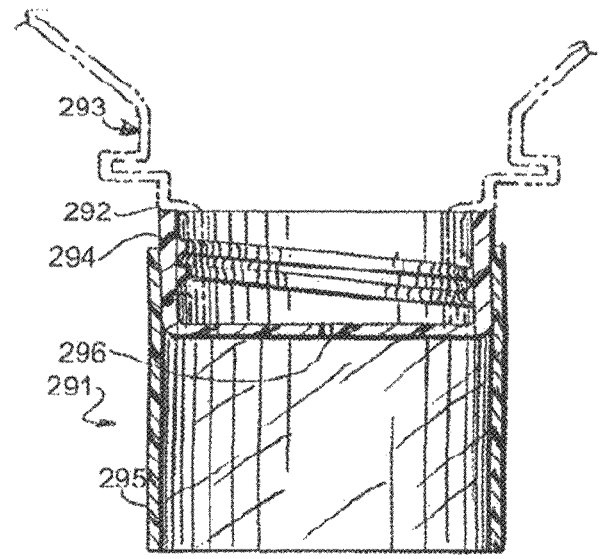
FIG. 19   FIG. 20

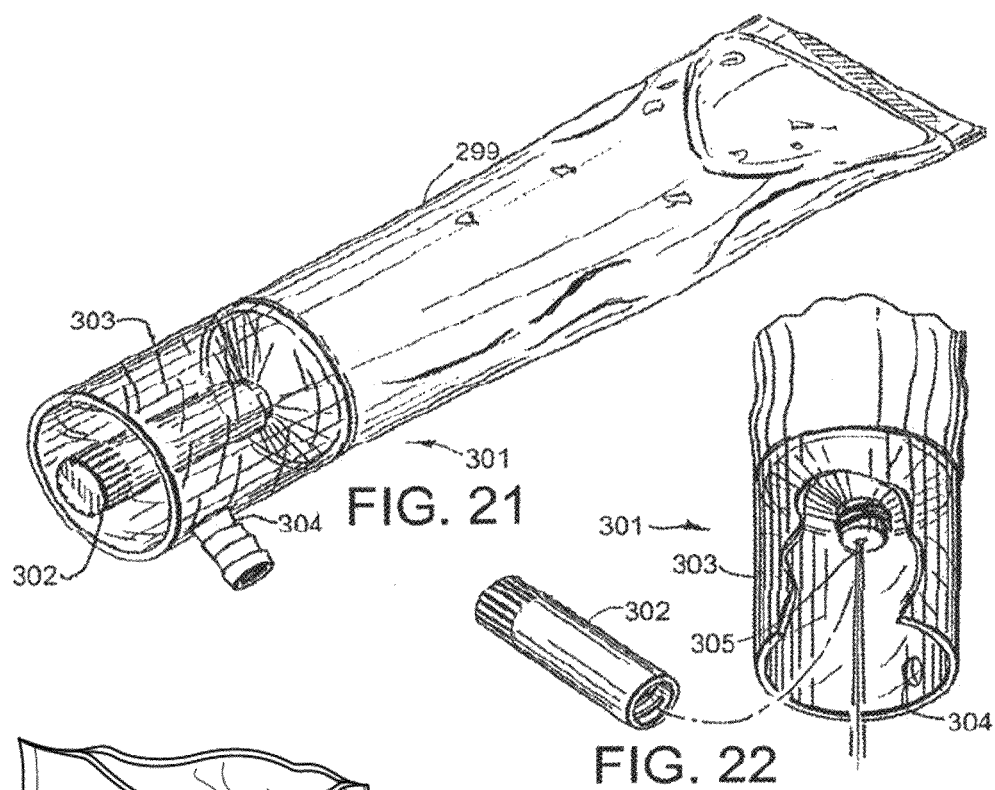
FIG. 21
FIG. 22
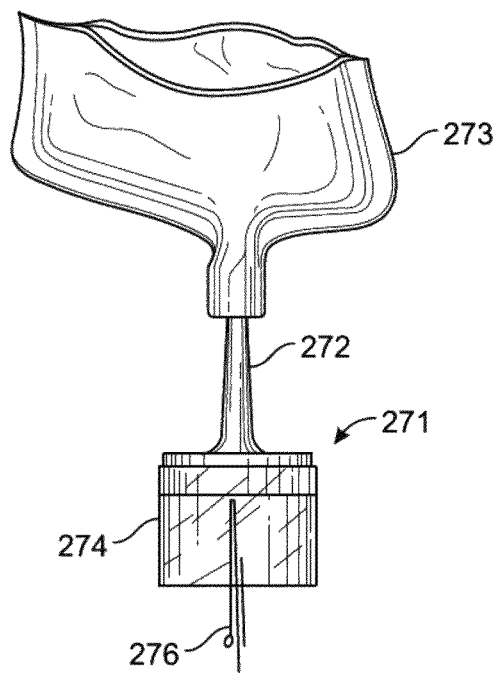
FIG. 23
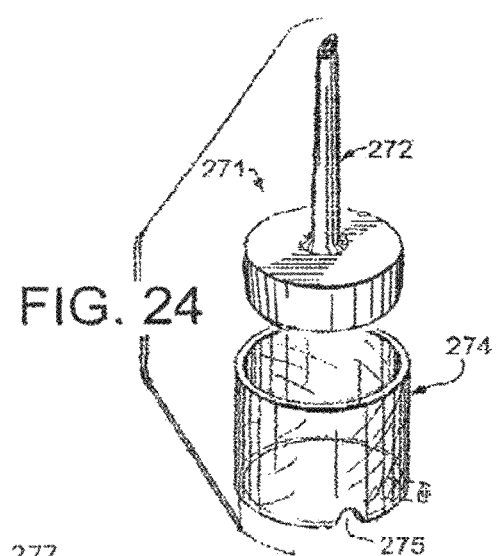
FIG. 24
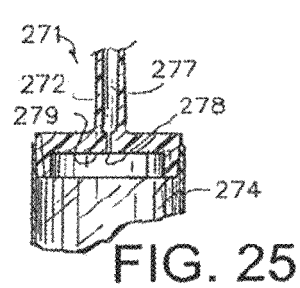
FIG. 25

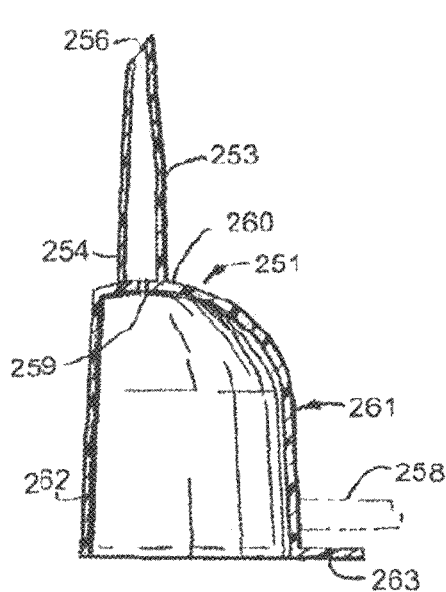
FIG. 30
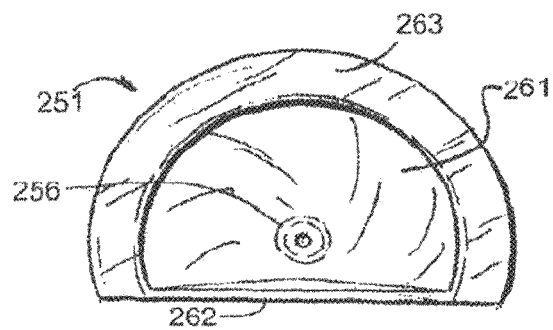
FIG. 31
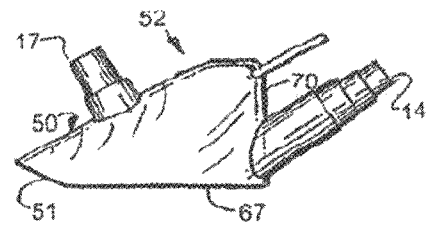
FIG. 32
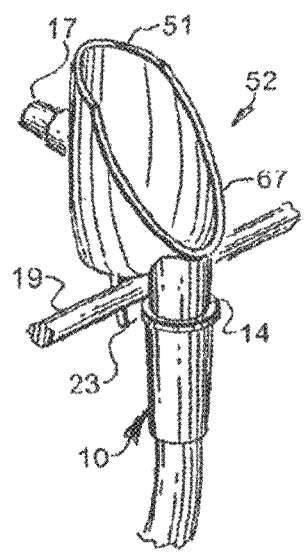
FIG. 34
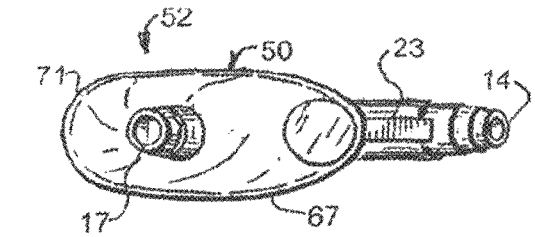
FIG. 33
FIG. 35

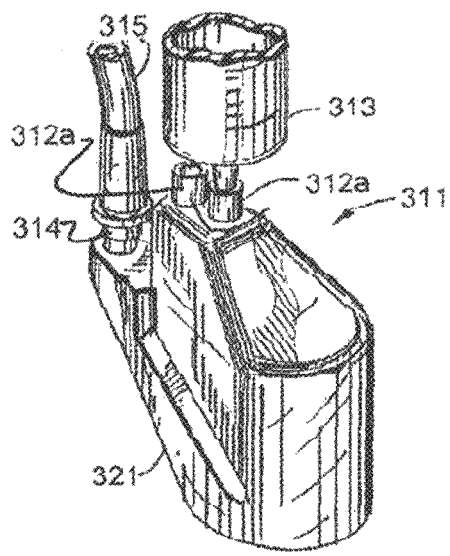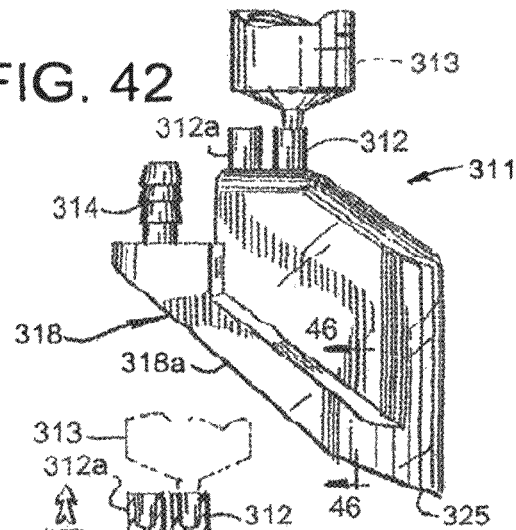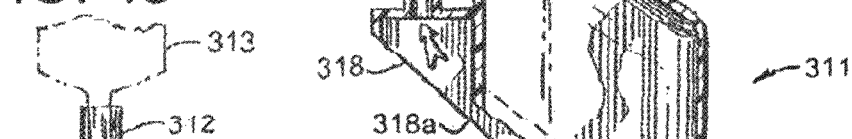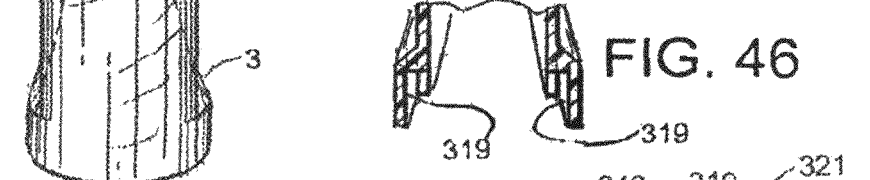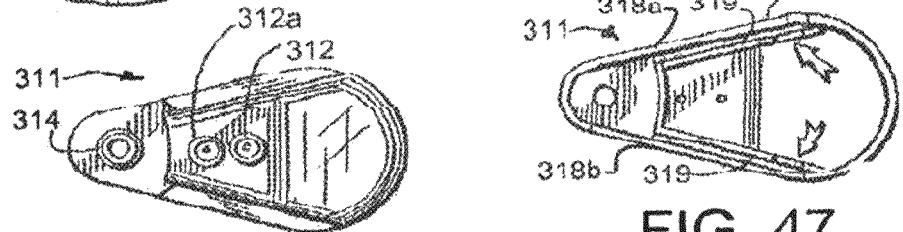

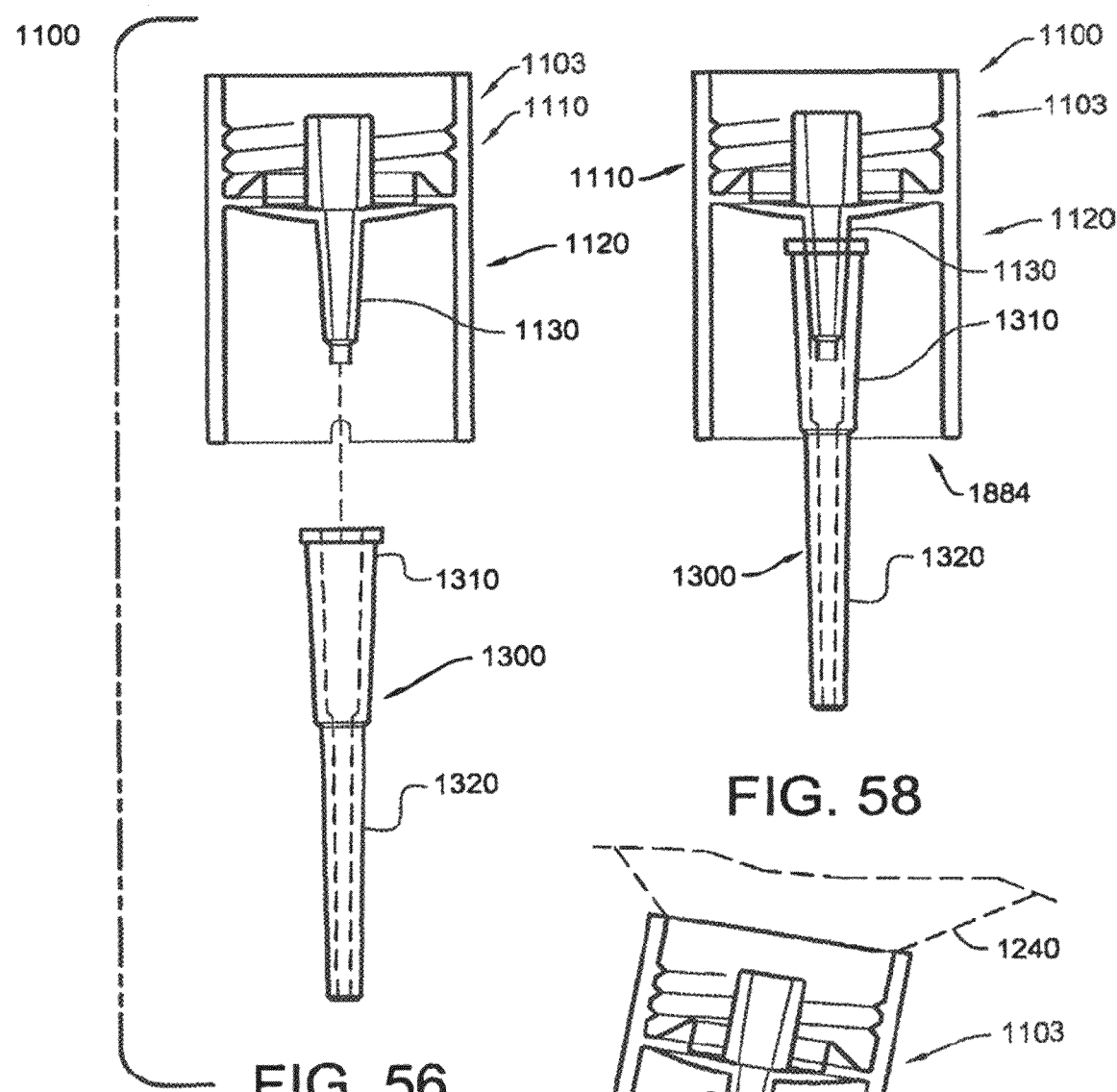
FIG. 56
FIG. 58
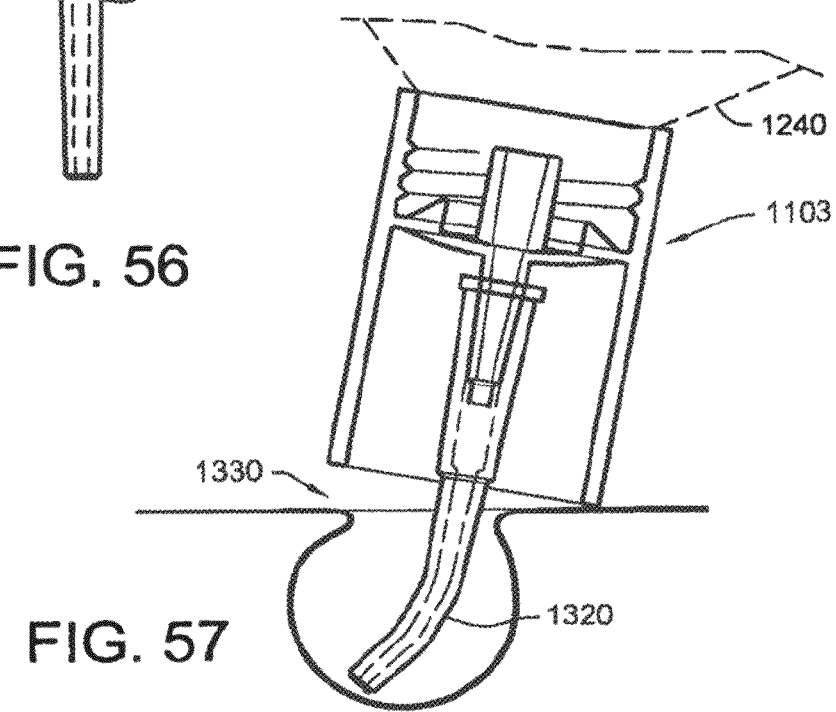
FIG. 57

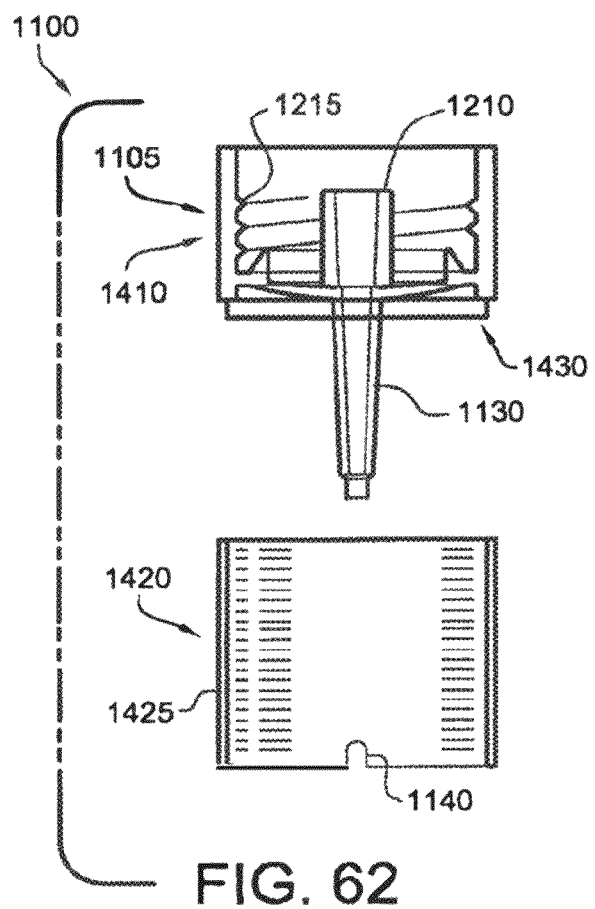
FIG. 62
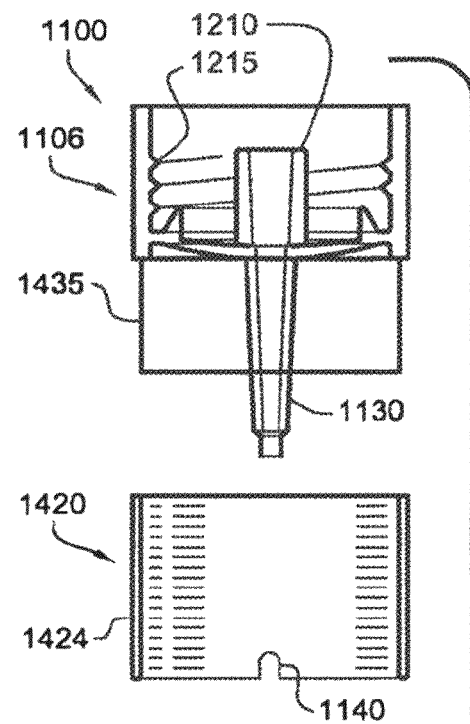
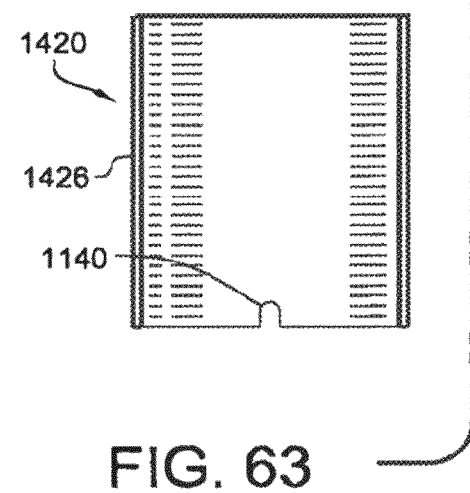
FIG. 63

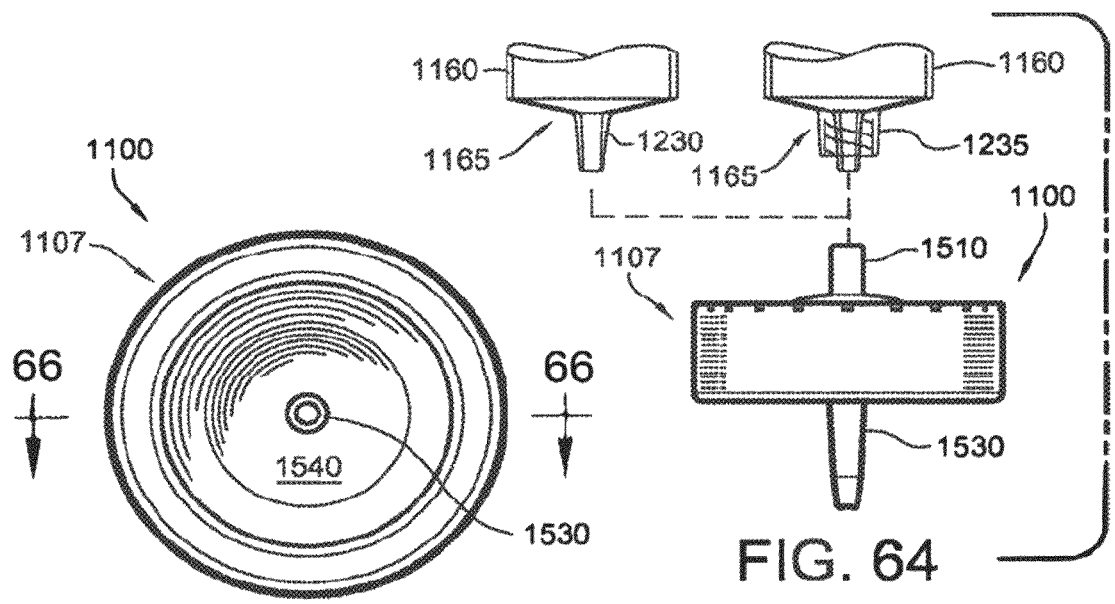
FIG. 65
FIG. 64
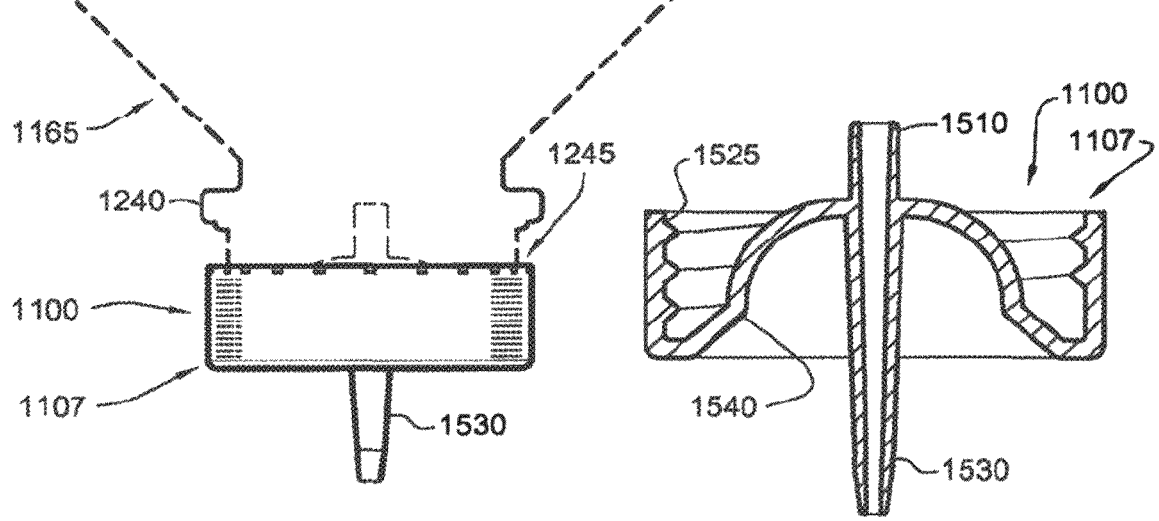
FIG. 67
FIG. 66

ABSCESS IRRIGATION SYSTEMS

REFERENCE TO RELATED APPLICATIONS

The present application is related to, and claims priority from, as a continuation application, U.S. patent application Ser. No. 16/596,347, filed on Oct. 8, 2019, now U.S. Pat. No. 11,083,835, which is a continuation of U.S. patent application Ser. No. 16/197,480, filed on Nov. 21, 2018, now U.S. Pat. No. 10,576,619, which is a continuation application of U.S. patent application Ser. No. 14/296,651, filed on Jun. 5, 2014, now U.S. Pat. No. 10,363,356, which is a continuation application of U.S. patent application Ser. No. 12/851,476, filed on Aug. 5, 2010, now U.S. Pat. No. 8,747,372, which claims the benefit of U.S. Provisional Application No. 61/325,756, filed Apr. 19, 2010, and U.S. Provisional Application No. 61/231,638, filed Aug. 5, 2009.

BACKGROUND

This invention relates to providing a medical system assisting more efficient and safer performance of medical procedures. More particularly, this invention concerns a medical system comprising apparatus and methods for improved irrigation and lavage. With respect to irrigation problems, when a patient has a wound, it is desirable to irrigate the wound with a solution such as normal saline. Presumably the dilution effect of the irrigation will wash out bacteria and debris and prevent wound contamination, infection, and scarring. The more fluid, the greater the degree of success in prevention. A higher pressure of irrigation could also help remove bacteria and push out unwanted debris. Unfortunately, when using large volumes or high amounts of pressures, there is a high likelihood of contaminated fluid spreading to unwanted surfaces, including splashing onto a health care provider or drenching the patient. This is undesirable as the risk of spreading of disease is heightened and there are undesirable effects of getting a patient wet (for example, a trauma patient with multiple wounds might be hypothermic from a large amount of irrigation fluid evaporating on his body, or a child with a facial laceration might become hypothermic from the excess fluid wetting its clothing during the winter). The excess fluid will also soil laundry and require increased housekeeping services, using existing methods of irrigation. This is also an inconvenience for otherwise healthy patients. They may have to remove their clothing to prevent them from getting soaked. This may be uncomfortable for the patient in a busy emergency room; and the time necessary for the patient to disrobe would delay a doctor's or nurse's ability to treat such patient or other waiting patients more expeditiously. These disadvantages will decrease the incentive for an operator, such as a physician, to appropriately use optimal large volumes of irrigation fluid; and therefore the risk of wound complications will increase.

Additionally, with respect to abscesses, a typical treatment involves incision of the abscess and drainage. This invention further relates to abscess irrigation systems.

OBJECTS AND FEATURES OF THE INVENTION

A primary object and feature of the present invention is to provide systems overcoming the above-mentioned problems.

It is a further object and feature of the present invention to provide irrigation systems that may be connected with either to a squeezable wide mouth irrigation fluid bottle or with a syringe providing a single useful tool for irrigation of multiple wound types. Another object and feature of the present invention is to provide a splash shield. Yet another object and feature of the present invention is to provide a splatter shield.

Another object and feature of the present invention is to provide an irrigation system having a splash shield and a nozzle extending beyond the splash shield. Another object and feature of the present invention is to provide such an irrigation system having an adjustable nozzle length. Another object and feature of the present invention is to provide an abscess irrigation system having an adjustable shield length.

Another object and feature of the present invention is to provide irrigation systems that are sealed so as not to drip when connected to irrigation fluid sources. Another object and feature of the present invention is to provide irrigation systems that are transparent so an irrigation-fluid administrator is able to view the irrigation process.

A further primary object and feature of the present invention is to provide such a system that is efficient, inexpensive, and handy. Other objects and features of this invention will become apparent with reference to the following descriptions.

SUMMARY OF THE INVENTION

In accordance with another preferred embodiment hereof, this invention provides an irrigation system comprising: at least one body comprising at least one first end, at least one second end, and at least one inner hollow having at least one first volume wherein such at least one second end is open to such at least one inner hollow forming at least one shield; at least one first irrigation source connector to connect such at least one body, at such at least one first end, to at least one squeezable wide mouth irrigation fluid bottle; at least one second irrigation source connector to connect such at least one body to at least one syringe, such at least one second irrigation source connector comprising at least one tubular member projecting in a direction toward such at least one first end; at least one irrigation fluid port to dispense fluid from such at least one squeezable wide mouth irrigation fluid bottle or such at least one syringe. Moreover, it provides such an irrigation system wherein such at least one second irrigation source connector comprises a tapered interior portion structured and arranged to make a luer-type connection with at least one irrigation source. Additionally, it provides such an irrigation system wherein such at least one second irrigation source connector is structured and arranged to fit at least one syringe having a slip fit luer-type connection. Also, it provides such an irrigation system wherein such at least one second irrigation source connector is structured and arranged to fit at least one syringe having a locking luer-type connection. In addition, it provides such an irrigation system wherein such at least one second irrigation source connector is structured and arranged to fit at least one syringe having a slip fit luer-type connection and at least one syringe having a locking luer-type connection. And, it provides such an irrigation system wherein such at least one at least one irrigation fluid port projects into such at least one inner hollow. Further, it provides such an apparatus wherein such at least one first irrigation source connector comprises at least one washer structured and arranged to form a seal when such at least one first irrigation source connector is connected to at least one squeezable wide mouth irrigation fluid bottle. Even further, it provides such an irrigation system wherein such at least one shield further comprises at least one aperture. Moreover, it provides such an irrigation system wherein such at least one shield is transparent. Additionally, it provides such an irrigation system wherein such at least one shield further comprises at least one void having a height substantially greater than its width. Also, it provides such an irrigation system wherein such at least one shield further comprises at least one void sized to permit insertion and manipulation of a syringe needle. In addition, it provides such an irrigation system further comprising at least one removable extension nozzle which, when attached to such at least one irrigation fluid port, extends beyond such at least one second end. And, it provides such an irrigation system wherein such at least one removable extension nozzle is flexible. Further, it provides such an irrigation system wherein such at least one removable extension nozzle is cuttable.

In accordance with another preferred embodiment hereof, this invention provides an irrigation system comprising: at least one body comprising at least one first end, at least one second end, and at least one inner hollow having at least one first volume wherein such at least one second end is open to such at least one inner hollow forming at least one shield; at least one dividing structure separating such at least one first end from such at least one second end; wherein such at least one dividing structure comprises at least one aperture; at least one aperture-insertable member comprising at least one nozzle portion; wherein, when such at least one at least one aperture-insertable member is inserted into such at least one aperture, such at least one nozzle portion projects into such at least one inner hollow. Even further, it provides such an irrigation system wherein such at least one aperture-insertable member further comprises at least one syringe connectable portion. Moreover, it provides such an irrigation system wherein such at least one body further comprises at least one squeezable wide mouth irrigation fluid bottle connector to connect such at least one body, at such at least one first end, to at least one squeezable wide mouth irrigation fluid bottle. Additionally, it provides such an irrigation system wherein such at least one aperture-insertable member comprises at least one larger-than-aperture portion to secure such at least one aperture-insertable member in such at least one aperture. Also, it provides such an irrigation system wherein such at least one syringe connectable portion comprises at least one tapered interior portion structured and arranged to make at least one luer-type connection with at least one syringe. In addition, it provides such an irrigation system wherein such at least one syringe connectable portion is structured and arranged to fit at least one syringe having a slip fit luer-type connection. And, it provides such an irrigation system wherein such at least one syringe connectable portion is structured and arranged to fit at least one syringe having a locking luer-type connection. Further, it provides such an irrigation system wherein such at least one syringe connectable portion is structured and arranged to fit at least one syringe having a slip fit luer-type connection and is also is structured and arranged to fit at least one syringe having a locking luer-type connection. Even further, it provides such an irrigation system wherein such at least one nozzle portion, when such at least one aperture-insertable member is inserted into such at least one aperture, extends beyond such at least one second end. Moreover, it provides such an irrigation system wherein such at least one nozzle portion is flexible. Additionally, it provides such an irrigation system wherein such at least one nozzle portion is cuttable. Also, it provides such an irrigation system wherein such at least one shield comprises at least one aperture. In addition, it provides such an irrigation system wherein such at least one dividing structure is positioned closer to such at least one second end than to such at least one first end. And, it provides such an irrigation system wherein such at least one squeezable wide mouth irrigation fluid bottle connector comprises at least one washer structured and arranged to form a seal when such at least one squeezable wide mouth irrigation fluid bottle connector is connected to at least one squeezable wide mouth irrigation fluid bottle.

In accordance with another preferred embodiment hereof, this invention provides an irrigation system comprising: at least one body comprising at least one first end, at least one first connector to connect such at least one body, at such at least one first end, to at least one squeezable wide mouth irrigation fluid bottle, and at least one nozzle projecting in a direction away from such at least one first end; at least one shield connector; at least one shield comprising at least one inner hollow, such at least one shield attachable to such at least one shield connector; wherein when such at least one shield is attached to such at least one shield connector, such at least one nozzle extends into such at least one shield. Further, it provides such an irrigation system wherein such at least one shield connector is sized to permit position selection of such at least one shield. Even further, it provides such an irrigation system wherein such at least one nozzle extends beyond such at least one shield connector. Moreover, it provides such an irrigation system wherein such at least one nozzle extends beyond such at least one shield connector and such at least one shield when such at least one shield is attached to such at least one shield connector. Additionally, it provides such an irrigation system wherein such at least one nozzle does not extend beyond such at least one shield when such at least one shield is attached to such at least one shield connector.

In accordance with another preferred embodiment hereof, this invention provides an irrigation system comprising: at least one syringe connector; at least one fluid output port in fluid communication with such at least one syringe connector; at least one shield having a dome-shaped configuration comprising at least one open end, at least one inner surface, and at least one outer surface, such at least one shield surrounding such at least one fluid output port; wherein such at least one fluid output port extends beyond such at least one open end of such at least one shield. Also, it provides such an irrigation system further comprising at least one tube situated within such at least one at least one fluid port used to lengthen the effective length of such at least one fluid output port. In addition, it provides such an irrigation system wherein such at least one tube is flexible. And, it provides such an irrigation system wherein such at least one tube is cuttable. Further, it provides such an irrigation system wherein such at least one syringe connector comprises at least one female luer taper. Even further, it provides such an irrigation system wherein such at least one shield is transparent. Even further, it provides such an irrigation system further comprising at least one bottle connector. Even further, it provides such an irrigation system further comprising at least one cap structure surrounding such at least one shield, such at least one cap structure structured and arranged to connect such irrigation system to at least one bottle.

In accordance with another preferred embodiment hereof, this invention provides a wound irrigation system comprising: at least one transparent and rigid hollow cup-shaped shield having at least one open lower end and at least one closed upper end and at least one inner surface and at least one outer surface; at least one conduit extending through such at least one outer surface and into such at least one transparent and rigid hollow cup-shaped shield in such at least one closed upper end, such at least one conduit having at least one top end configured to accept at least one irrigation source and generally narrowing as extending downwardly through such at least one inner surface to at least one bottom end; and at least one aperture, substantially adjacent such at least one conduit, extending through such at least one closed upper end of such at least one transparent and rigid hollow cup-shaped shield. Even further, it provides such a wound irrigation system wherein such at least one irrigation source connects by at least one luer-type connection. Even further, it provides such a wound irrigation system wherein such at least one irrigation source comprises at least one syringe. Even further, it provides such a wound irrigation system wherein such at least one irrigation source comprises at least one syringe.

In accordance with another preferred embodiment hereof, this invention provides a method relating to preventing spraying or splatter of fluid from an injection site comprising the steps of: placing at least one shield having at least one open end and at least one inner hollow over at least one portion of tissue to be injected; injecting such at least one portion of tissue to be injected; and shielding a user from any spraying or splattering resulting from the injection using such at least one shield. Even further, it provides such a method wherein such at least one shield comprises at least one aperture suitable to insert and manipulate at least one injecting device.

In accordance with another preferred embodiment hereof, this invention provides each and every novel feature, element, combination, step and/or method disclosed or suggested herein.

BRIEF DESCRIPTION OF THE DRAWINGS

FIG. 17 is a sectional view through the center of the embodiment of FIG. 15 showing structural details and showing its fit in the illustrated bottle (which is in dotted lines).

FIG. 18 is a side view of a splash shield with an end cap attached on the top end and an end cap detached from the bottom end of splash shield.

FIG. 19 is an exploded perspective view of yet another preferred embodiment of the splash shield of the present invention, showing the end of an irrigation bottle, a bottle adapter to control the irrigation stream, and a tubular splash shield element.

FIG. 20 is a sectional view of the embodiment of FIG. 19 illustrating the details with the splash shield connected to the bottle (shown in dotted lines).

FIG. 21 is a perspective view of a preferred embodiment of a combined splash shield and irrigation squeeze tube according to the present invention.

FIG. 22 is a partial perspective view of the embodiment of FIG. 21, partially cut away to show its use with cap removed.

FIG. 23 is a front view illustrating yet another preferred embodiment of a splash shield according to the present invention, showing a spike connector attached to a squeeze bag and also fitted into a cylindrical splash shield element.

FIG. 24 is a perspective view of the embodiment of FIG. 23, showing the spike connector separated from the cylindrical splash shield element.

FIG. 25 is a partial sectional view showing the connection details with the spike connector attached to the cylindrical splash shield element.

FIG. 30 is sectional side view of the embodiment of FIG. 28 illustrating the structural details thereof.

FIG. 31 is a bottom view of the embodiment of FIG. 28.

FIG. 32 is a side elevation view of a preferred embodiment of the splash shield medical device of the present invention.

FIG. 33 is a top plan view of the embodiment of FIG. 32.

FIG. 34 is a perspective view of the embodiment of FIG. 32 showing it in a restrained position.

FIG. 35 is a side sectional view of the embodiment of FIG. 32, illustrating its operation.

FIG. 41 is a perspective view of yet another preferred embodiment of a splash shield according to the present invention.

FIG. 42 is a side view of the embodiment of FIG. 41, shown attached to the irrigation syringe.

FIG. 43 is a front view of the embodiment of FIG. 41, with the irrigation syringe in dotted lines.

FIG. 44 is a side sectional view of the embodiment of FIG. 41 showing the structural details and fluid flow directions.

FIG. 45 is a top view of the embodiment of FIG. 41.

FIG. 46 is a partial sectional view through the section 46-46 of FIG. 42.

FIG. 47 is a bottom view of the embodiment of FIG. 41.

FIG. 56 shows a side view of an abscess irrigation system, illustrating a nozzle extension, according to an alternately preferred embodiment of the present invention.

FIG. 57 shows a side view of the abscess irrigation system of FIG. 56, illustrating use of the nozzle extension.

FIG. 58 shows a side view of the abscess irrigation system of FIG. 56, illustrating attachment of the nozzle extension.

FIG. 62 shows a side view of an irrigation system, illustrating at least one detachable shield, according to an alternately preferred embodiment of the present invention.

FIG. 63 shows a side view of an irrigation system, illustrating at least one adjustable-height shield, according to an alternately preferred embodiment of the present invention.

FIG. 64 shows a side view of an irrigation system, illustrating at least one multiple-type connector, according to an alternately preferred embodiment of the present invention.

FIG. 65 shows a bottom view of the irrigation system of FIG. 64.

FIG. 66 shows the sectional view 66-66 of FIG. 65.

FIG. 67 shows a side view of the irrigation system of FIG. 66, illustrating attachment to at least one fluid bottle.

DETAILED DESCRIPTION OF THE BEST MODES AND PREFERRED EMBODIMENTS OF THE INVENTION

Figure 1:
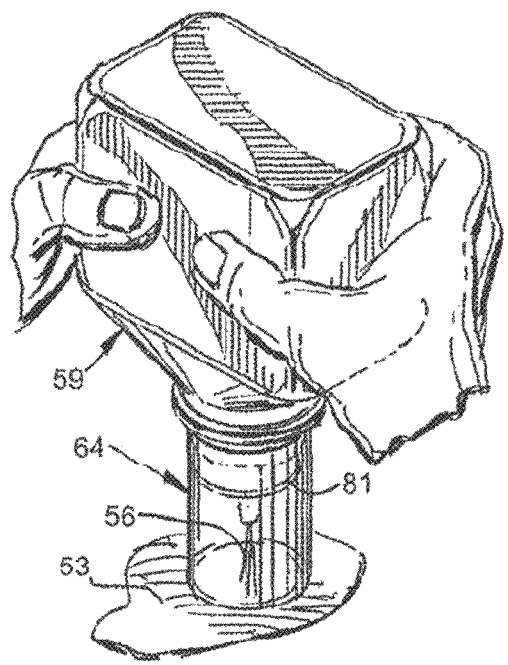
FIG. 1 is a perspective view of a preferred embodiment of a splash shield system according to the present invention, and showing use with an irrigation squeeze bottle.

FIG. 1 is a perspective view of a preferred embodiment of a splash shield system according to the present invention, showing use of splash shield 64 attached to wide mouth irrigation squeeze bottle 59. Preferably, wide mouth irrigation squeeze bottle 59 comprises a standard high volume plastic squeeze bottle of sterile fluid (sometimes also referred to herein as irrigation fluid), as shown. Preferably, wide mouth irrigation squeeze bottle 59 comprises a volume of at least about 250 cc. Preferably, wide mouth irrigation squeeze bottle 59 comprises a volume less than about 1750 cc. Preferably, wide mouth irrigation squeeze bottle 59 comprises bottle neck finish portion 30, as shown. Preferably, bottle neck finish portion 30 comprises an inner diameter between about ¾ inches and about 1¼ inches, most preferably between about ⅘ inches and about 1¼ inches. Preferably, bottle neck finish portion 30 comprises an outer diameter between about ⅘ inches and about 1¾ inches. Preferably, wide mouth irrigation squeeze bottle 59 comprises a standard wide mouth wound irrigation squeeze bottle, such as, for example, wide mouth wound irrigation squeeze bottles manufactured and/or distributed by Baxter Healthcare Corporation (or Baxter International, Inc.) of Deerfield, 11. (sometimes referred to herein as BAXTER), Abbott Laboratories of Abbott Park, Il. (and related company Hospira Worldwide, Inc., of Lake Forest, Il.) (sometimes referred to herein as ABBOTT), or B. Braun Medical, Inc. of Allentown, PA (and related company McGaw, Inc., of Irvine, Ca.)(sometimes referred to herein as MCGAW). Preferably, when wide mouth irrigation squeeze bottle 59 is squeezed, fluid 56 is squirted onto flesh 53 (also referred to herein as body surface) of the patient, as shown. It is preferred that a wide mouth irrigation fluid bottle is used to reduce time filling up a basin or bath by pouring the contents of the irrigation fluid bottle into such basin or bath and then filling up a syringe from such basin or bath. Even if a syringe that has dimensions that may allow a user to insert the syringe into a wide mouth bottle is used, the syringe volume capacity is such that it will be time consuming and cumbersome to fill and refill the syringe to adequately irrigate the wound. Syringe shields cannot be inserted into a wide mouth bottle. To use a syringe shield with a wide mouth irrigation fluid bottle, a user must disconnect and reconnect the shield to the syringe each time the user needs to refill the syringe with irrigation fluid. Again, this is time consuming, cumbersome, and inefficient. Using the splash cap system of the present invention overcomes these problems.

Figure 2:
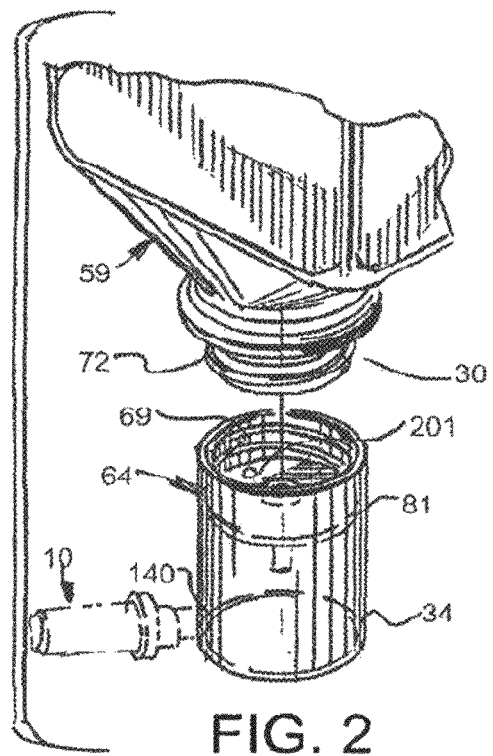
FIG. 2 is an exploded perspective view of the embodiment of FIG. 1, and further showing (in dotted lines) the structure of another preferred alternate embodiment using vacuum evacuation of irrigation fluid through a port situated near the plane of irrigation.
Figure 3:
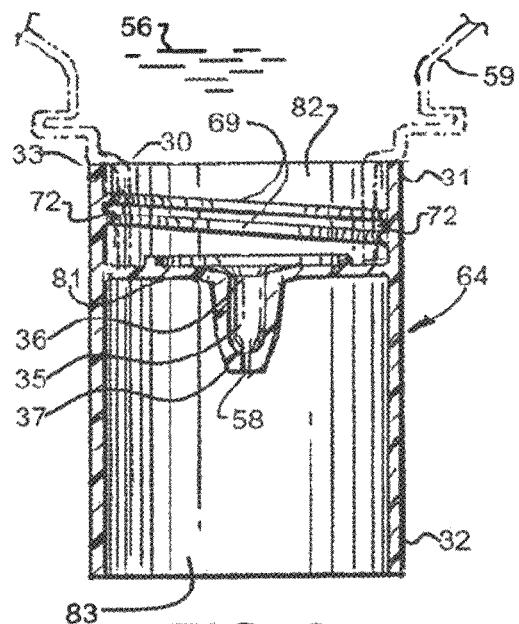
FIG. 3 is a sectional view of the embodiment of FIG. 1, illustrating details of preferred structure.

FIG. 2 shows a preferred embodiment of the present invention with wide mouth irrigation squeeze bottle 59 detached from splash shield 64. FIG. 3 is a sectional view of the embodiment of FIG. 1, illustrating details of a preferred structure. Preferably, splash shield 64 is transparent, as shown. Preferably, splash shield 64 comprises first end 31 and second end 32, as shown. Preferably, partition 81 divides first end 31 from second end 32, as shown. Preferably first end 31 comprises irrigation-source connector 33, as shown. Preferably, irrigation-source connector 33 comprises an inner diameter between about 4/5 inches and about 1¾ inches, most preferably between about 1.4 inches and about 1.6 inches, most preferably between about 1.3 inches and 1.6. Based on the type of connector desired, one may prefer an inner thread-to-thread diameter of about 1.3 inches over about 1.4 inches in cases where a thicker thread is desired. Preferably splash shield 64, including irrigation-source connector 33, partition 81, and inner hollow 83, consist of one monolithic piece. Preferably splash shield 64 is sterile.

Preferably, irrigation-source connector 33 comprises threads 69, as shown. Preferably, threads 69 comprise helical threads, as shown. Preferably second end 32 comprises inner hollow 83 as shown. Preferably, bottle neck finish portion 30 of wide mouth irrigation squeeze bottle 59 comprises threads 72, as shown. Preferably, threads 72 comprise male threads, as shown. Preferably, threads 72 comprise helical threads, as shown (embodying herein a bottle structured and arranged to contain irrigation fluid, such bottle comprising, a neck, wherein such neck comprises external threads structured and arranged to connect with a bottle cap) structured and arranged to couple with threads 69 (such threads embodying herein threads structured and arranged to provide a threaded connection with the source of irrigation fluid; and further embodying herein wherein such threads comprise internal threads structured and arranged to connect with external threads on a neck of a irrigation fluid bottle; and further embodying wherein such irrigation-source connecter comprises threads structured and arranged to provide a threaded connection; and further embodying herein an adapter structured and arranged to allow a connection between such body and such source of irrigation fluid) within inner hollow 82 of splash shield 64 to form a tight connection. Preferably, irrigation-source connector 33 is structured and arranged to connect to standard wide mouth wound irrigation squeeze bottles, such as, for example, those manufactured by BAXTER, ABBOT, or MCGAW. Upon reading the teachings of this specification, those with ordinary skill in the art will now understand that, under appropriate circumstances, considering such issues as cost of manufacture, compatibility, market demand, etc., other connection arrangements, such as, for example, non-helical threads, female threads, luer-type connections, non-threaded connections, snap on connections, etc., may suffice.

Preferably, partition 81 comprises orifice nozzle 58 for directing a stream of fluid from the irrigation source (such as, for example, wide mouth irrigation squeeze bottle 59) toward flesh 53 (embodying herein a body, having a first end and a second end wherein such first end is open to a first hollow portion of such body and such second end is open to a second hollow portion of such body; an irrigation-source connecter structured and arranged to connect such body, adjacent the first end, to a source of irrigation fluid; a partition, between such first hollow portion and such second hollow portion; wherein such partition comprises at least one nozzle structured and arranged to direct at least one stream of the irrigation fluid towards the wound; wherein such splash shield system is structured and arranged in such manner as to protect the user from contact with the irrigation fluid; and further embodying herein wherein such adapter comprises a nozzle structured and arranged to direct a stream of the irrigation fluid towards the wound).

Preferably, nozzle 58 protrudes from partition 81, as shown. Preferably, nozzle 58 protrudes from partition 81 a distance between about 0.005 inches to about 1 inch, as shown. Preferably nozzle 58 comprises at least one passageway 35 with at least one cross-sectional area, which decreases from at least one inlet port 36 of said at least one nozzle to at least one outlet port 37 of said at least one nozzle, forming at least one venturi passageway 35, as shown. Preferably, the length of passageway 35 is between about 0.005 inches to about 1 inch. Preferably, splash shield 64 comprises a cylindrical exterior wall portion 34 (see FIG. 2), as shown, wherein "cylindrical", as used throughout this specification, is defined in the broad mathematical sense as a surface traced by a straight line moving parallel to a fixed straight line and intersecting a fixed planar closed curve. Preferably cylindrical exterior wall portion 34 is substantially round. Preferably inner hollow 83 comprises a substantially round cylindrical portion, as shown (embodying herein a body having a first end and a second end, and a cylindrical exterior wall and irrigation-source connector structured and arranged to connect such body, at such first end, to a source of irrigation fluid; wherein such body comprises at least one inner hollow; wherein such second end, is open to such at least one inner hollow; wherein such splash shield system is structured and arranged in such manner as to protect the user from contact with the irrigation fluid; and further embodying herein wherein such cylindrical exterior wall is substantially round; and such at least one inner hollow comprises a substantially round cylinder). Upon reading the teachings of this specification, those with ordinary skill in the art will now understand that, under appropriate circumstances, considering such issues as intended use, user preference, cost of manufacture, etc., other splash shield shape arrangements, such as, for example, non-cylindrical portions, conical shaped portions, asymmetrical shaped portions, etc., may suffice.

According to the preferred embodiment shown in FIG. 1, there is preferably a single nozzle for irrigating flesh 53 with fluid 56, as shown. According to the preferred embodiment shown in FIG. 2, partition 81 preferably comprises at least one additional hole 201 to facilitate irrigating flesh 53 with multiple streams of fluid 56 (wherein such partition further comprises, at least one hole through such partition (in addition to such nozzle)). Thus, when bottle 59 is attached and squeezed, fluid 56 is forced into and through orifice nozzle 58 (and also, through hole 201), as shown.

FIG. 2 also shows (in dotted lines) the structure of another preferred alternate embodiment using vacuum evacuation of irrigation fluid by vacuum line 10 through a port 140 situated near (as shown) the plane of irrigation (embodying herein an output opening structured and arranged to allow suctioning excess irrigation fluid from within such body).

Using the invention with a standard wide mouth irrigation bottle with a port approximately the size of a luer tip opening, one can generate a pressure similar to that of the outer diameter of an 18-gauge needle. Though this may seem counter-intuitive to some, this larger luer sized opening has a diameter approximately 4 times the size of the smaller 18-gauge sized opening, and it is capable of generating a similar peak irrigation stream pressure. Although fluid discharge ports larger than 1.5 mm can provide advantages, fluid discharge ports larger than 4 mm may have disadvantages. Beyond a certain point the diameter of the fluid discharge port may become too large. The diameter of the port may become so large that fluid from the stream is wasted. For example, a stream of a diameter of more than 4 mm would waste a lot of fluid irrigating a more narrow laceration of 1 mm. Beyond a certain width a port that is too wide might not be able to generate the desired irrigation pressures using a standard manual squeeze bottle. 4 mm is the approximate size of catheter tip piston syringe openings. Catheter tip plunger syringes have been shown to generate a pressure of at least 4 psi.

In the medical literature there is much debate over the ideal pressure to irrigate a wound. For eye wounds it is desirable to limit the pressure, but increase the volume of fluid. For wounds treated in the hospital and clinic setting, some authors recommend at least 4 psi and others recommend at least 7 psi. Some recommend no more than 8 psi of pressure and other recommend no more than 15 psi of pressure. Typically in the operating room higher pressure devices are used. In chronic wound care settings frequently low pressures are used. The ideal medical irrigation device or method is one that is simple, inexpensive and can achieve a variety of different pressure ranges and allows the user to choose the pressure or range which they judge to be optimal.

When using devices with that generate higher pressured streams it is desirable to have an adequately sealed system to permit more efficient generation of pressures without loss of pressure through leaks. Leakage would require more energy to be used to generate a higher pressure in the system and therefore of the irrigation stream. In the case of manually squeezed irrigation bottle, leakage of the system may make some pressures unattainable by manual pressure that otherwise would have been attainable.

Another problem with leakage of manually squeezed irrigation bottle system is that the leaks may cause irrigation fluid to drain or spray out around the collar of the wide mouth irrigation bottle connector. Along with reducing the pressure achievable in the system, such a leakage may cause a messy situation. Fluid may drip on the outside of the irrigation shield. If the shield is transparent, the leaked fluid drops or streaks may obstruct the view through the transparent splash shield.

It is therefore desirable to have a shielded irrigation device that has a liquid tight seal on at least one irrigation bottle finish.

Figure 4:
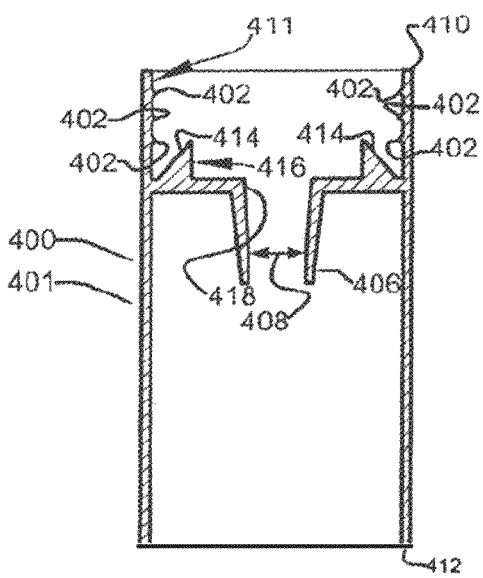
FIG. 4 is a sectional view of another preferred embodiment of a splash shield system according to the present invention.

FIG. 4 is a sectional view through splash shield 400. Preferably, splash shield 400 comprises body 401, as shown. Preferably, body 401 consists essentially of one unitary, monolithic piece, as shown. Preferably, body 401 comprises transparent plastic. Preferably, transparency provides minimal distortion and maximum clarity so that the wound can be easily viewed through body 401 (allowing the user to accurately aim the irrigation stream). Preferably, the irrigation of the wound can be easily viewed from the side of transparent body 401 or from above body 401. Maximum clarity can generally be achieved more effectively with rigid material. Preferably, body 401 comprises first end 410 and second end 412, as shown. Preferably, first end 410 comprises irrigation source connector 411 (at least embodying herein at least one squeezable wide mouth irrigation fluid bottle connector structured and arranged to connect such at least one body), as shown. Splash shield 400 caps a wide mouth irrigation fluid bottle when connected to a wide mouth irrigation fluid bottle. Preferably, second end 412 comprises inner hollow 404, as shown. Preferably, second end 412 comprises at least one transparent portion. Preferably, first end 410 is in fluid communication with second end 412 via fluid discharge port 418 (also sometimes referred to herein as an irrigation fluid port), as shown. Preferably, fluid discharge port 418 comprises nozzle 406. Preferably, nozzle 406 protrudes into inner hollow 404, as shown. Preferably inner hollow 404 is structured and arranged to assist in containing fluid which is discharged from fluid discharge port 418 into inner hollow 404, as shown. Preferably, inner hollow 404 may temporarily contain greater than 25 ml of irrigation fluid when second end 402 is placed adjacent the flesh of a patient. Since a wide mouth irrigation fluid bottle dispenses a larger volume of irrigation fluid than, for example, a 20 cc handheld syringe, a larger shield capable of temporarily containing such volume of greater than 25 ml is preferred to properly irrigate the wound of a patient. It is desired that the volume of the shield be sufficient to contain a volume, temporarily, when the splash shield is adjacent the flesh or body surface of a patient so that a large volume of irrigation fluid from a large area fluid port may flow to irrigate a wound. A large fluid port preferably has a large area for discharge of fluid. For purposes of this disclosure, a large area fluid port is not greater than a port having a diameter of 1 mm. Preferably, such fluid port has a diameter of 1.5 mm. A further advantage of the larger volume inner hollow is that it permits a user to direct irrigation fluid to a wound. When using 20 cc syringe to irrigate a wound, constant refilling is necessary to apply large volumes. This is inefficient when time may be of the essence in emergency care situations. If the inner hollow volume is too small, insufficient irrigation fluid will reach the wound and will diminish the protective effect of the splash shield because, for example, the low volume splash shield will need to be raised to accommodate further irrigation fluid. The height of inner hollow 404 may also be important in providing a user with a reasonable and comfortable way to look through the shield of splash cap 400 when the splash cap 400 is connected to a wide mouth irrigation squeeze bottle, inverted, and used to irrigate a wound. Preferably, inner hollow 404 helps protect a user from fluid that is discharged from fluid discharge port 418 and splashing fluid that results when the fluid impacts the wound (contaminated irrigation fluid), etc. Preferably, fluid discharge port 418 has a diameter 408 of at least 1.5 mm. Preferably, fluid discharge port 418 has a diameter 408 of at least 2 mm. Preferably, fluid discharge port 418 has a diameter 408 of at least 2.5 mm.

Figure 5:
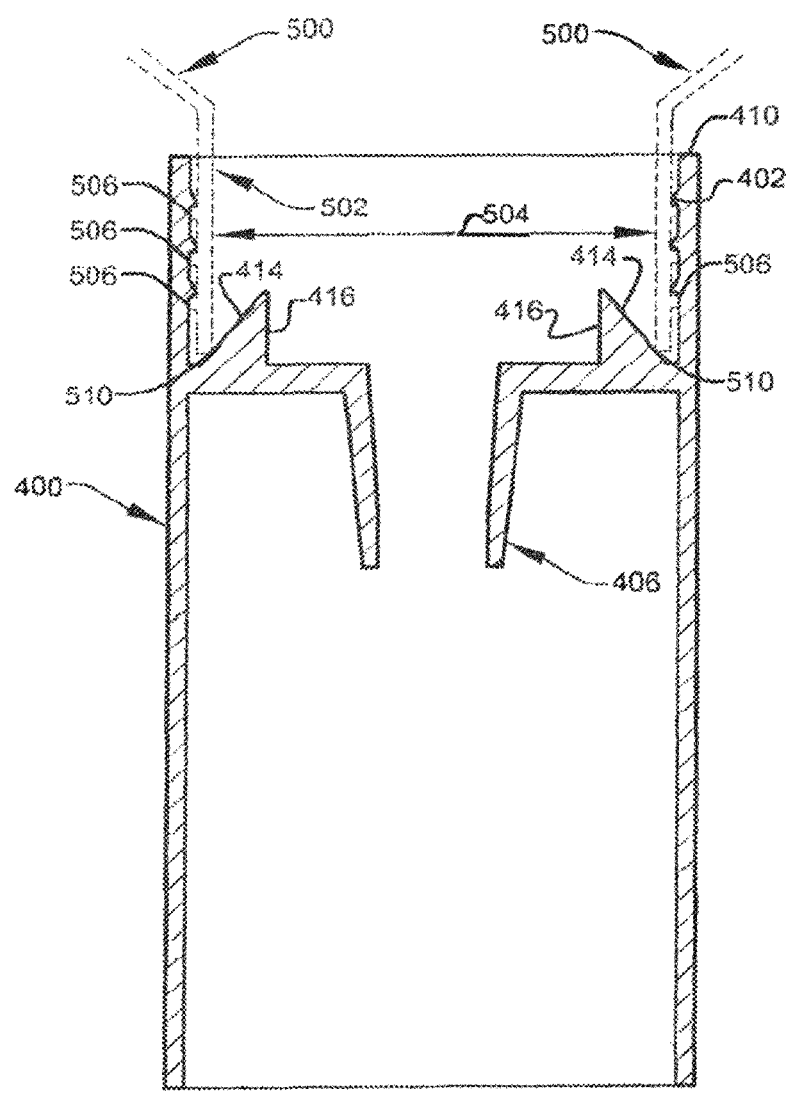
FIG. 5 is an enlarged view of the embodiment of FIG. 4 attached to a bottle (which is shown in dotted lines) with a wide inner diameter bottle finish.
Figure 6:
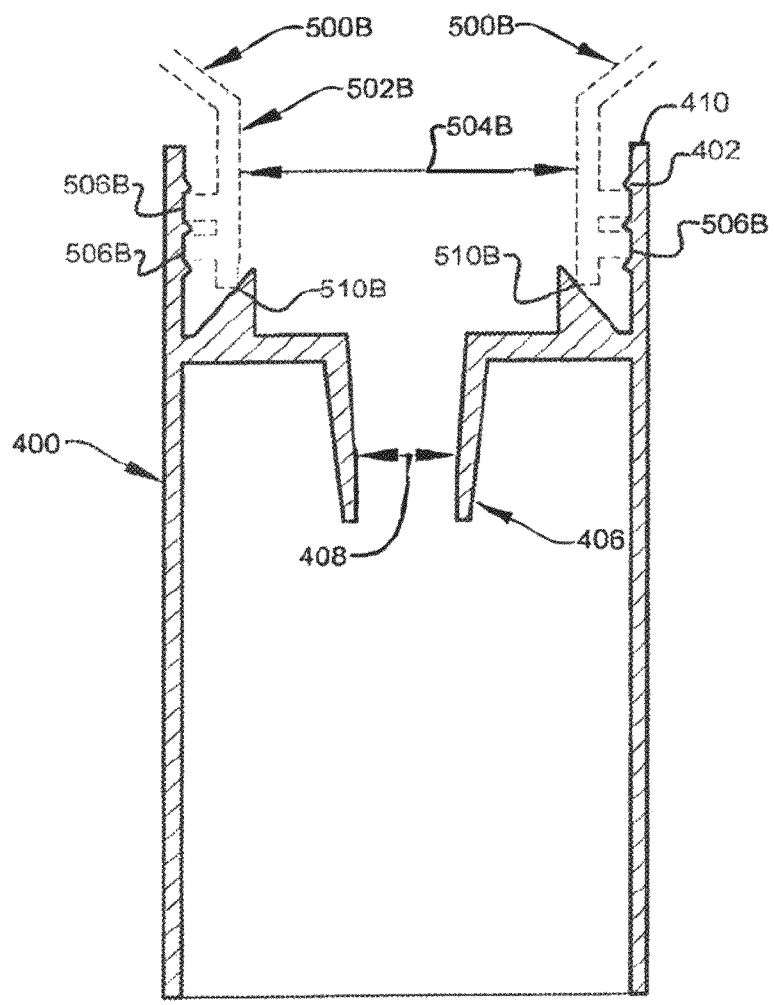
FIG. 6 is an enlarged view of the embodiment of FIG. 4 attached to a bottle (which is shown in dotted lines) with an inner diameter bottle finish narrower than the bottle shown in FIG. 5.

Preferably, irrigation source connector 411 is structured and arranged to accommodate a range of bottle finish sizes. Comparing FIG. 5 and FIG. 6, it can be seen how splash shield 400 can accommodate attaching to wide mouth wound irrigation squeeze bottles with different sized bottle finish portions. FIG. 5 shows splash shield 400 connected to bottle 500 with a relatively wider diameter bottle finish inner diameter 504, as shown. FIG. 6 shows splash shield 400 connected to bottle 500B with a relatively narrower diameter bottle finish inner diameter 504B, as shown.

Referring to FIG. 5, preferably, irrigation source connector 411 comprises threads 402, as shown. Preferably, threads 402 are structured and arranged to provide a threaded connection with threads 506 on the bottle finish 502 of a wide mouth wound irrigation squeeze bottle 500. Preferably, threads 402 have standard thread dimensions. Preferably, threads 402 comprise 1¼-6 UNC thread dimension. Preferably, threads 402 comprise 1¼-6 UNC coarse thread dimension. Preferably, threads 402 comprise helical threads with at least 2 turns, more preferably at least 2.5 turns. Less than 2 turns increases the likelihood of cross threading problems, and is therefore less preferable. More than 2.5 turns helps prevent cross threading and improves universal sealing to a variety of different sized bottle finishes (such as the different dimensions of bottle finishes for standard wound irrigation squeeze bottles manufactured by BAXTER, ABBOT, and MCGAW.

Preferably, irrigation source connector 411 is structured and arranged to provide a liquid-tight seal so that when an irrigation source (e.g. a wide mouth wound irrigation squeeze bottle) is attached to the irrigation source connector 411, fluid can only escape through the fluid discharge port 418 (and fluid cannot escape through the connection, threads, etc.). Preferably, irrigation source connector 411 comprises ridge 416 (at least embodying herein at least one washer structured and arranged to form a seal when such at least one squeezable wide mouth irrigation fluid bottle connector is connected to at least one squeezable wide mouth irrigation fluid bottle), as shown. Preferably, ridge 416 comprises ridge outer surface 414, as shown. Preferably, ridge outer surface 414 is structured and arranged to seal against the inner diameter of a bottle neck finish portion. Preferably, ridge 416 is shaped with an external taper (slant/slope), as shown. Ridge 416 permits a liquid-tight seal without relying on resilient material so that splash shield 400 can be manufactured as one monolithic piece of rigid material to reduce cost. Preferably, liquid-tight seal 510 is achieved by contact between the inner diameter of the bottle finish and outer surface of ridge 416, as shown. Preferably, seal 510 is achieved by screwing splash shield 400 onto wide mouth wound irrigation squeeze bottle 500 (by engagement between threads 506 and threads 402) until the end of bottle finish 502 seats tightly on ridge outer surface 414 of ridge 416, as shown. Preferably, irrigation source connector 411 is structured and arranged so that seal 510 (and seal 510B, etc., for other size bottle finishes) remains liquid-tight (preventing leaking of fluid) at pressures of 4 pounds per square inch, preferably remaining liquid-tight at pressures of 7 pounds per square inch.

Comparing FIG. 5 and FIG. 6, it can be seen that for relatively wider diameter bottle finish inner diameter 504 (see FIG. 5), seal 510 occurs nearer the base of ridge 416 (where the ridge outer surface diameter is larger compared to the top). Whereas, for relatively narrower diameter bottle finish inner diameter 504B (see FIG. 6), seal 510B occurs nearer the top/apex of ridge 416 (where the ridge outer surface diameter is smaller compared to the base). Preferably, ridge outer surface 414 has a range of ridge outer surface diameters from greater than 1.2 inches near the base, to less than 1.14 inches near the top/apex of ridge 416, as shown. Preferably, irrigation source connector 411 is structured and arranged to accommodate and provide a liquid-tight seal for a range of bottle finish sizes. Preferably, irrigation source connector 411 is structured and arranged to universally fit and provide a liquid-tight seal for the different bottle finish dimensions of standard wound irrigation bottles manufactured by BAXTER, ABBOT, and MCGAW. It is noted that BAXTER standard wound irrigation bottles typically have an inner diameter of about 1.14 inches, while ABBOT standard wound irrigation bottles typically have an inner diameter of about 1.17 inches, and MCGAW standard wound irrigation bottles typically have an inner diameter of about 1.2 inches. By being able to universally fit any of the top three most popular manufacturers mentioned above, splash shield 400 is more convenient and efficient than a product that would only fit one specific bottle size. Further, splash shield 400 preferably fits to standard squeezable wide mouth irrigation fluid pour bottles which are designed to have an inner lip in addition to their wide mouth diameter to avoid irrigation fluid dripping while pouring such standard bottles.

According to an alternate preferred embodiment of the present invention ridge 416 comprises resilient material. According to another alternate preferred embodiment of the present invention ridge 416 can be supplemented and/or replaced by a washer, preferably made of resilient material, in order to achieve a liquid tight seal.

Figure 7:
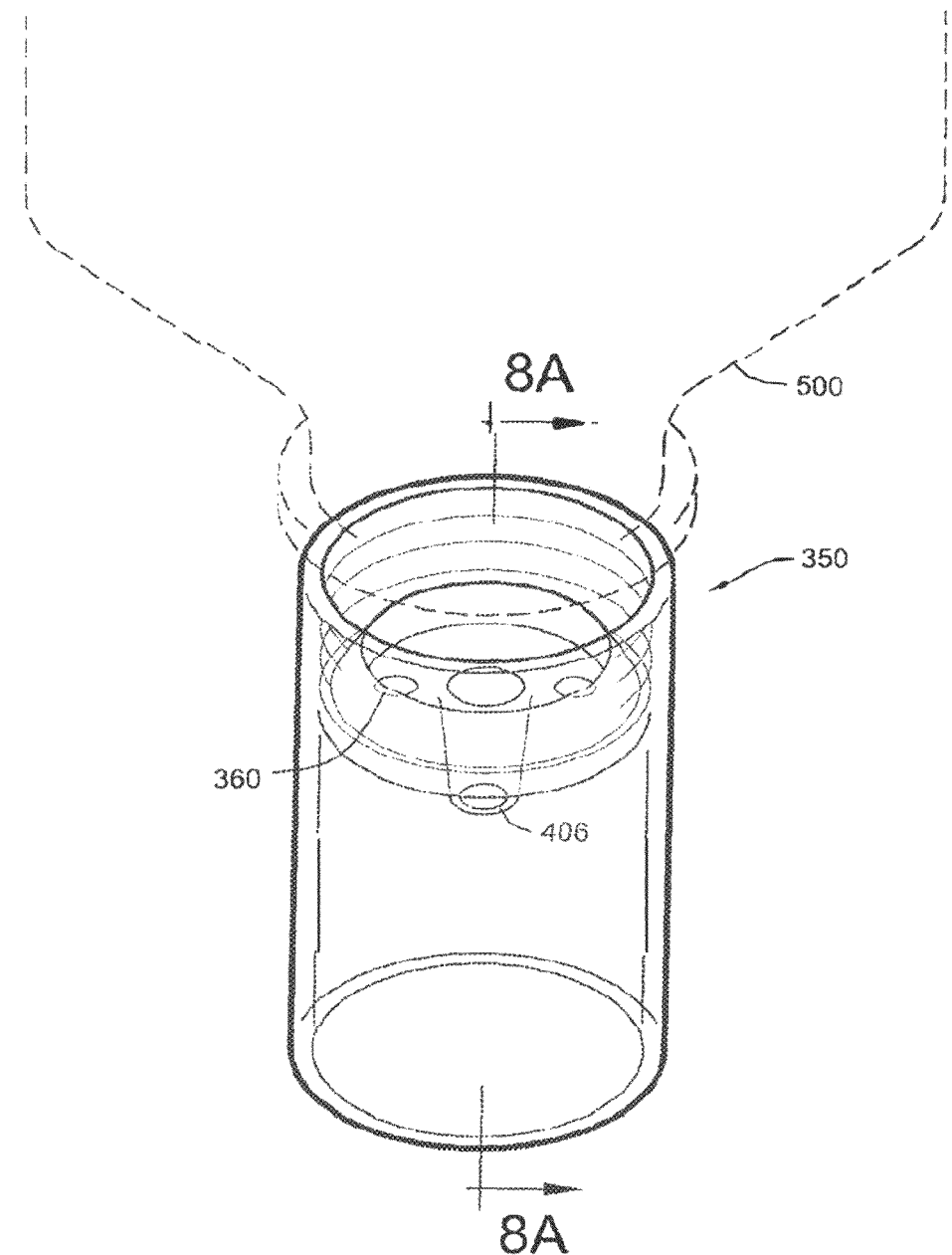
FIG. 7 shows a perspective view showing an alternate preferred embodiment of a splash shield system with multiple irrigation fluid discharge ports.
Figure 8A:
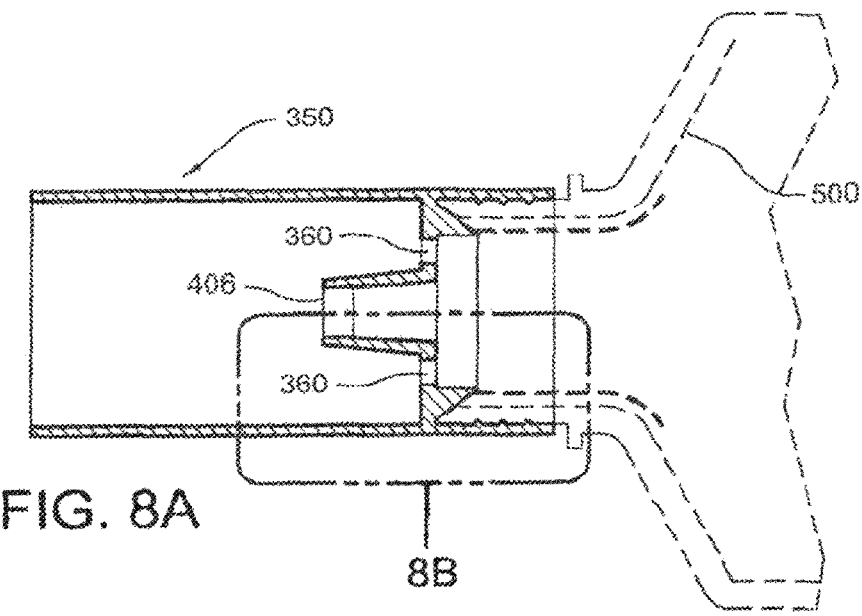
FIG. 8A shows a sectional view through the section 8A-8A of FIG. 7.
Figure 8B:
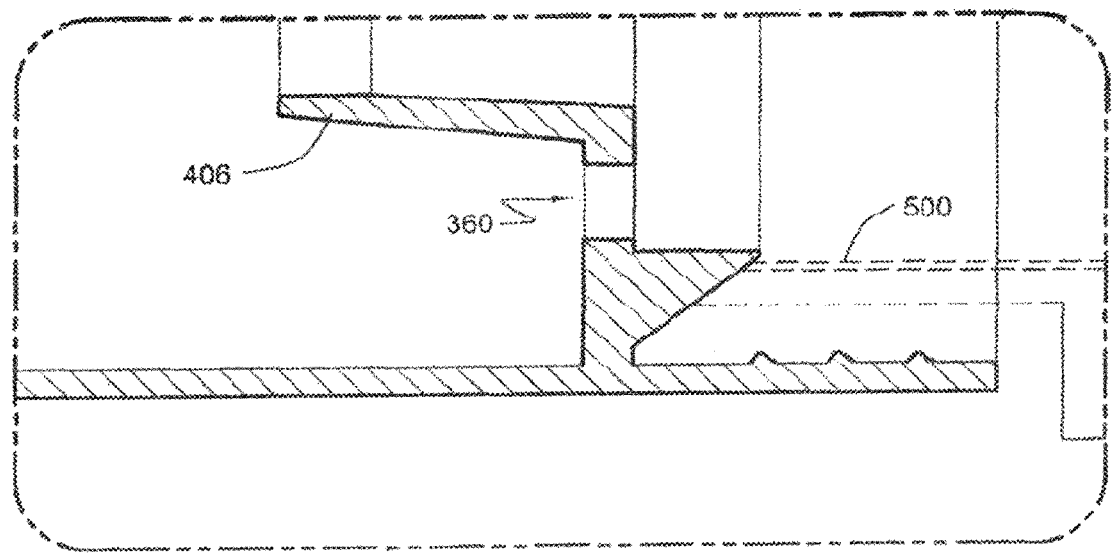
FIG. 8B shows a sectional view, magnified for clarity, of the section of FIG. 8A.

FIG. 7 shows a perspective view showing an alternate preferred embodiment of a splash shield system with multiple fluid discharge ports 360. FIG. 8A and FIG. 8B show a sectional view and blowup detail sectional view, respectively, of the embodiment of FIG. 7. Splash shield system preferably comprises splash shield 350. While splash shield 350 preferably comprises many elements of splash shield 400, splash shield 350 preferably further comprises multiple discharge ports 360. Discharge ports 360 preferably prevent over pressuring fluid discharge through nozzle 406.

Figure 9:
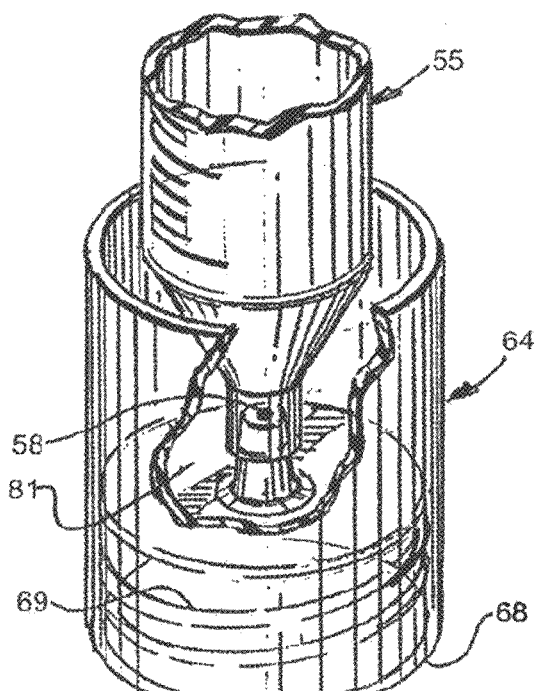
FIG. 9 is a perspective view illustrating the use of the splash shield of FIG. 1, inverted for use with a syringe.
Figure 10:
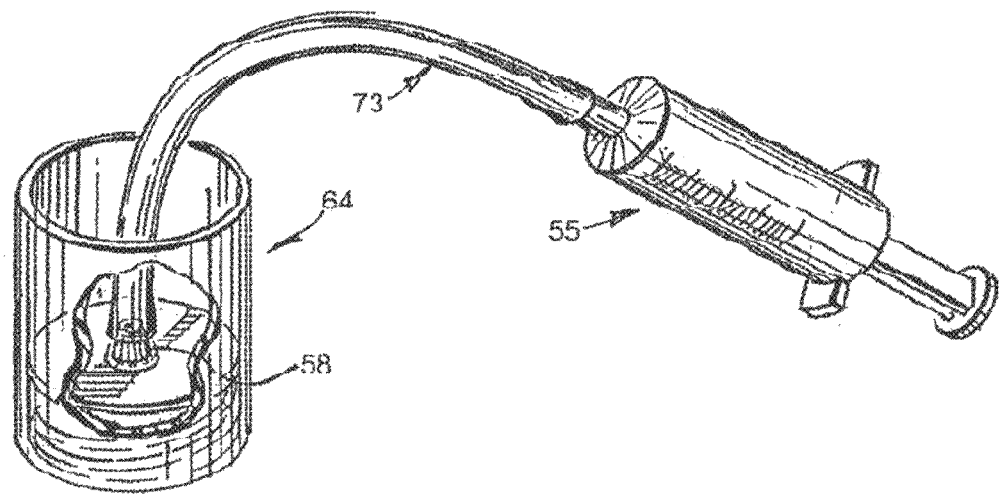
FIG. 10 is a perspective view illustrating the use of the splash shield of FIG. 9 using a syringe with connecting tubing.

FIG. 9 is a perspective view illustrating the use of the splash shield 64 of FIG. 1 inverted for use with a syringe 55. In this embodiment, the open unthreaded end of splash shield 64 receives a syringe 55 whose nozzle fits over the now protruding (from the former underside of partition 81) part of orifice nozzle 58, as shown. Thus, when syringe 55 discharges its fluid, the threaded portion 68 of splash shield 64 now acts as a splash shield. Similarly, FIG. 10 is a perspective view illustrating the use of the splash shield 64 "upside down" arrangement of FIG. 9 using a syringe 55 with connecting tubing 73, which tubing 73 is in this case connected over the protruding orifice nozzle 58.

Those with ordinary skill in the art, upon reading this specification (e.g., FIGS. 2, 7, and 9 and associated comments), will understand that one of applicant's preferred embodiments combines a syringe with an aperture useful, for example, in venting excess gases (typically air) when the combined syringe and splash shield are filled with irrigation fluid from an irrigation fluid source. Such preferred embodiment(s) herein embody: at least one transparent and rigid hollow cup-shaped shield having at least one open lower end and at least one closed upper end and at least one inner surface and at least one outer surface; at least one conduit extending through said at least one outer surface and into said at least one transparent and rigid hollow cup-shaped shield in said at least one closed upper end, said at least one conduit having at least one top end configured to accept at least one irrigation source and generally narrowing as extending downwardly through said at least one inner surface to at least one bottom end; and at least one aperture, substantially adjacent said at least one conduit, extending through said at least one closed upper end of said at least one transparent and rigid hollow cup-shaped shield.

Figure 11:
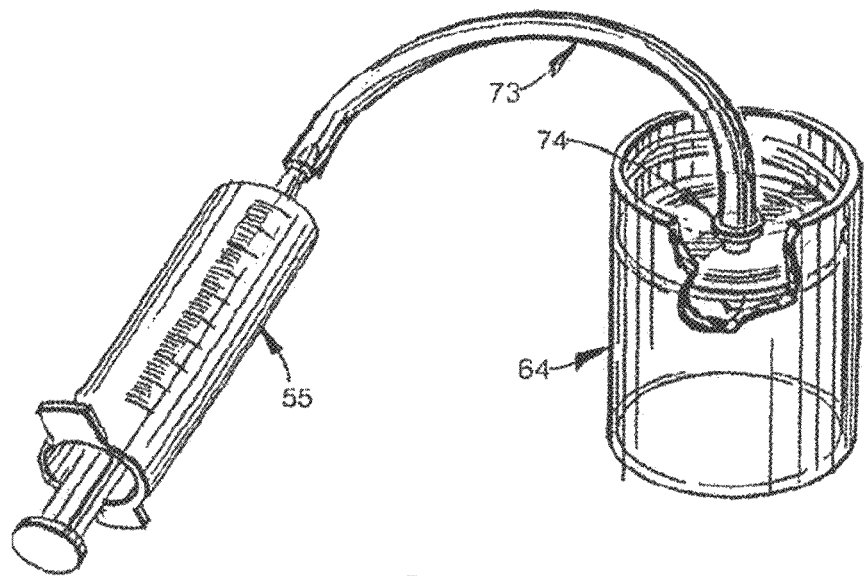
FIG. 11 is a perspective view illustrating the use of the splash shield of FIG. 1 using a syringe with connecting tubing and an adapter.
Figure 12:
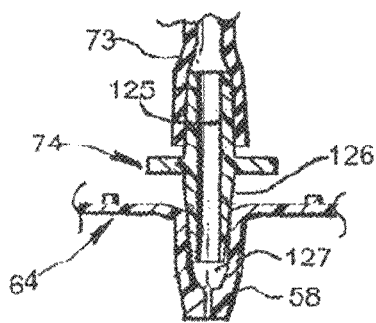
FIG. 12 is a sectional view of the adapter connection area of the embodiment of FIG. 11 illustrating the area detail.

FIG. 11 is a perspective view illustrating the use of the splash shield 64 of FIG. 1 using a syringe 55 with connecting tubing 73 and an adapter 74. FIG. 12 is a sectional view of the adapter 74 connection area of the embodiment of FIG. 11 illustrating the area detail. As shown, tubing 73 fits over an upper male portion 125 of the adapter 74 while a lower male portion 126 of the adapter 74 fits within the upper hollow 127 of orifice nozzle 58 (embodying herein wherein such adapter allows connection of such body to multiple varieties of such source of irrigation fluid). Preferably, upper hollow 127 also allows connection to an irrigation-source with a syringe tip (embodying herein wherein such irrigation-source connecter further comprises at least one adapter structured and arranged to provide a connection to a syringe tip).

Figure 13:
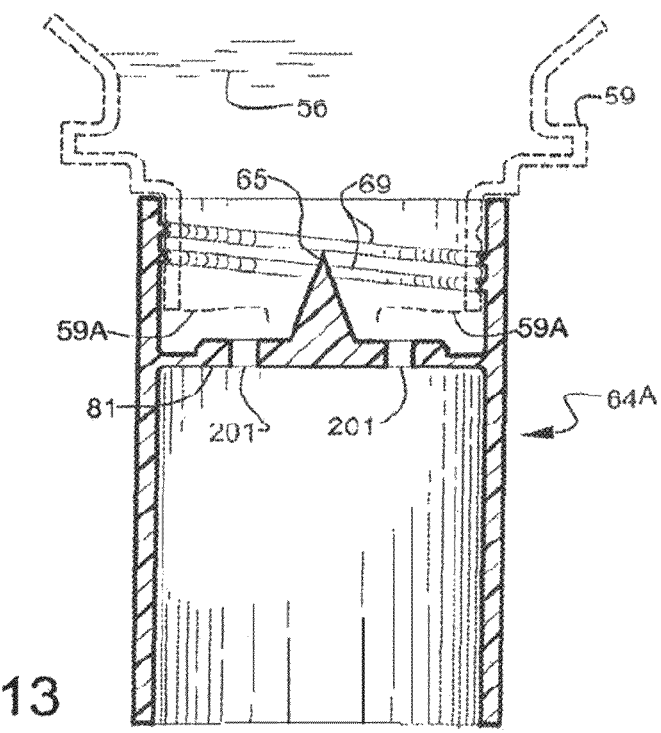
FIG. 13 is a sectional view of another preferred embodiment of a splash shield according to the present invention, showing a puncturing means for breaking the seal on a source of irrigation fluid.

FIG. 13 is a sectional view of yet another preferred embodiment of a splash shield 64A according to the present invention, meshed with an irrigation squeeze bottle 59, illustrating details of preferred structure. Preferably, splash shield 64A has a puncturer 65, as shown (embodying herein a body structured and arranged to assist in protecting a user from contact with irrigation fluid directed at a patient's wound; an irrigation-source connecter structured and arranged to connect such body, at a first end of such body, to a source of irrigation fluid; wherein such irrigation-source connecter comprises a puncturer structured and arranged to puncture at least one barrier between such body and the source of irrigation fluid and further embodying wherein such puncturer comprises a spike). As splash shield 64A is meshed with bottle 59, bottle membrane 59A (which acts as a barrier to fluid escaping the bottle 59) is punctured by puncturer 65, which permits fluid to exit from bottle 59. Below the threads 69 of splash shield 64A is internal partition 81 sealing the open/bottom end of splash shield 64A except for hole(s) 201. Preferably, puncturer 65 does not puncture bottle membrane 59A until after sufficient connection between the bottle 59 and the splash shield 64A is made to provide a sufficient seal preventing fluid from leaking from the meshed connection. Preferably, puncturer 65 punctures a bottle membrane 59A when the meshed connection between splash shield 64A and bottle 59 is already engaged, but not yet fully and completely seated, preferably when the meshed connection is approximately half-way complete. Thus, when bottle 59 is attached and squeezed, fluid 56 is forced into and through hole(s) 201.

Figure 14:
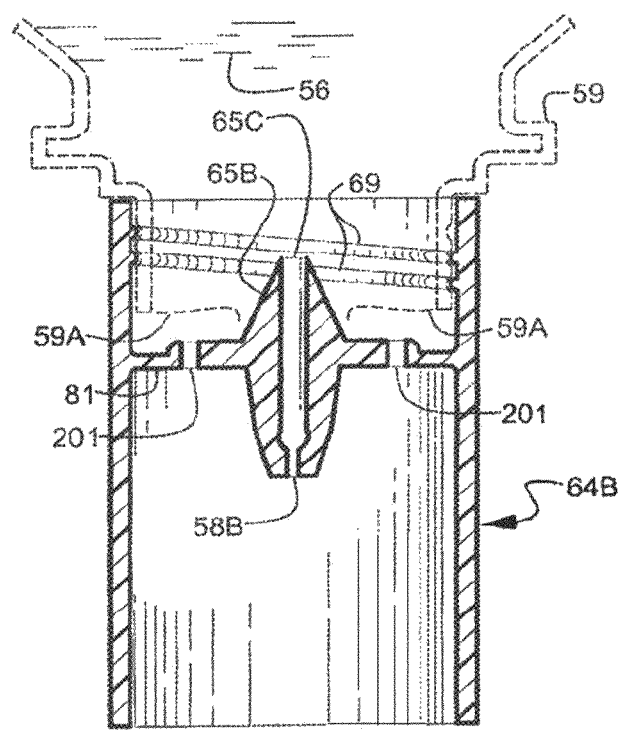
FIG. 14 is a sectional view of another preferred embodiment of a splash shield according to the present invention, showing a puncturing means with integral fluid transport means.

FIG. 14 is a sectional view of yet another preferred embodiment of a splash shield 64B according to the present invention, meshed with an irrigation squeeze bottle 59, illustrating details of preferred structure. Preferably, splash shield 64B has a puncturer 65B. As splash shield 64B is meshed with bottle 59, bottle membrane 59A is punctured by puncturer 65B, which permits fluid to exit from bottle 59. One or more fluid channel(s) 65C in puncturer 65B permits fluid 56 to exit from bottle 59 into orifice nozzle 58B (embodying herein wherein such spike comprises at least one opening structured and arranged to transport the irrigation fluid from the source of irrigation fluid to such body). Below the threads 69 of splash shield 64B is internal partition 81 sealing the open/bottom end of splash shield 64B except for orifice nozzle 58B for directing a stream toward flesh 53. It is noted, that one or more additional hole(s) 201 may be optionally found going through partition 81 in order to increase irrigation flow to a wound. Preferably, puncturer 65B does not puncture bottle membrane 59A until after sufficient connection between the bottle 59 and the splash shield 64B is made to provide a sufficient seal preventing fluid from leaking from the meshed connection. Preferably, puncturer 65B punctures bottle membrane 59A when the meshed connection between splash shield 64B and bottle 59 is already engaged, but not yet fully and completely seated, preferably when the meshed connection is approximately half-way complete. Thus, when bottle 59 is attached and squeezed, fluid 56 is forced through the fluid channel(s) 65C and through orifice nozzle 58 (and also, optionally, through optional hole(s) 201), as shown.

Figures 15, 16:
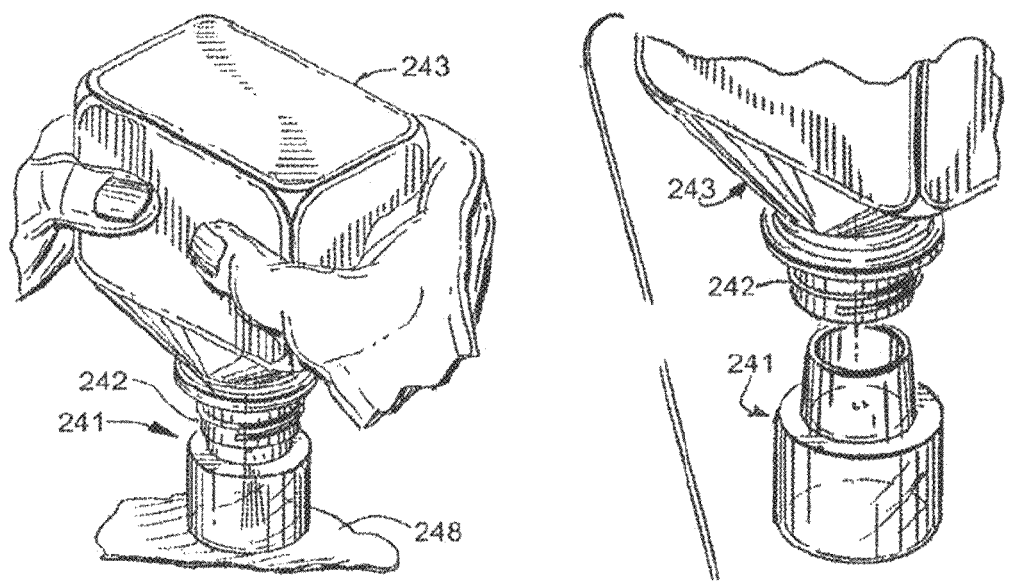
FIG. 15 is a perspective view of another preferred embodiment of a splash shield according to the present invention, which splash shield is shown fitted into the neck of a bottle of the type containing irrigation fluid.
FIG. 16 is a perspective view of the embodiment of FIG. 15 shown detached from the illustrated bottle.

FIG. 15 is a perspective view of another preferred embodiment of a splash shield 241 according to the present invention, which splash shield 241 is shown fitted into the neck 242 of a bottle 243 of the type containing irrigation fluid. FIG. 16 is a perspective view of the splash shield 241 of FIG. 15 shown detached from the illustrated bottle 243. FIG. 17 is a sectional view through the center of the splash shield 241 of FIG. 15 showing structural details and showing its fit in the illustrated bottle 243 (which is in dotted lines). Splash shield 241 (as shown best in FIG. 17) is stepped from a larger-diameter cylindrical portion 244 to a smaller-diameter portion 245 that is sized with external taper to friction fit as shown within neck 242 of bottle 243 (in dotted lines in FIG. 17). Thus, for example, squeezing of a squeeze bottle 243 brings irrigation fluid into upper portion 245, from where it may be forced through a hole 246 in dividing surface 247 to impinge upon skin portion 248 (see FIG. 15) with lower portion 244 acting to shield say, a user, from fluid or debris from a wound on skin portion 248. FIG. 18 is a side view of a splash shield with an end cap 332 attached on the top end and an end cap 332 detached from the bottom end of splash shield 330. Preferably, end cap 332 assists in protecting internal sterility of the splash shield. End cap 332 also creates a closed pocket within splash shield, which can be used for example to store other items such as wound treatment products and devices.

FIG. 19 is an exploded perspective view of yet another preferred embodiment of the splash shield 291 of the present invention, showing the end 292 of an irrigation bottle 293, a bottle adapter 294 to control the irrigation stream, and a tubular splash shield element 295. FIG. 20 is a sectional view of the splash shield 291 of FIG. 19 illustrating the details with the splash shield 291 connected to the bottle 293 (shown in dotted lines). As shown, to use the splash shield 291, it is preferred to friction fit adapter 294 over the end 292 of bottle 293, and to friction fit splash shield element 295 over the bottom of adapter 294. Then fluid from bottle 293 may be forced into adapter 294, through hole 296, and into the tubular splash shield element areas for wound irrigation.

FIG. 21 is a perspective view of a preferred embodiment of a combined splash shield and irrigation squeeze tube 301 according to the present invention. FIG. 22 is a partial perspective view of the irrigation squeeze tube 301 of FIG. 21, partially cut away to show its use with cap 302 removed. Toothpaste-type squeeze tube portion 299 has a built-in or a removable transparent wound irrigation shield portion 303. An outlet 304 to allow fluid egress or to allow attachment to a vacuum source (not shown) may be optionally provided for the advantages enumerated previously. Cap 302 is made long enough for removal or attachment to tube portion 299 with shield portion 303 in place. In operation, the tube portion 299 is squeezed, thus forcing irrigation fluid onto a wound, as previously set forth generally. Having a removable shield portion 303 is preferred if cap 302 is to be provided with nozzle 305 adaptations or adaptors (as taught previously herein) that allow modulation and that must be accessed easily in a sterile fashion, particularly if a simple, cheap, and easily available component such as a transparent plastic PVC tubing were used.

FIG. 23 is a front view illustrating yet another preferred embodiment of a splash shield 271 according to the present invention, showing a spike connector 272 attached to a squeeze bag 273 and also fitted into a cylindrical splash shield element 274. FIG. 24 is a perspective view of the splash shield 271 of FIG. 23, showing the spike connector 272 separated from the cylindrical splash shield element 274. FIG. 25 is a partial sectional view showing the connection details with the spike connector 272 attached to the cylindrical splash shield element 274. Spike connector 272 is a component of the type commonly used in creating an IV spike dripping chamber for modulating the administration of IV fluid through IV tubing, as shown (embodying herein wherein such spike comprises an IV-spike connecter, unitary with such body). Splash shield element 274 may be made from standard PVC tubing to create an easily produced IV spike connector wound irrigation splash shield 271. By using simple available components in a new configuration and method, the tool investment would be minimized. It would also provide users with familiar equipment and parts that would reduce apprehension over using a new device. Providing this splash shield 271 permanently connected would provide significant advantages in some situations as described above. There may be an optional outlet contour or aperture 275 (see FIG. 24) which can function as an exit opening for effluent irrigation fluid or for the attachment of a vacuum connector. In addition, the tubing comprising splash shield element 274 may be flexible to prevent discomfort and trauma and to facilitate a better seal against the skin. When splash shield 271 is connected to bag 273, squeezed irrigation fluid 276 is forced through spike conduit 277 and through hole 278 in dividing surface 279, from where it enters attached splash shield element 274 for the described usages in wound irrigation.

Figure 26:
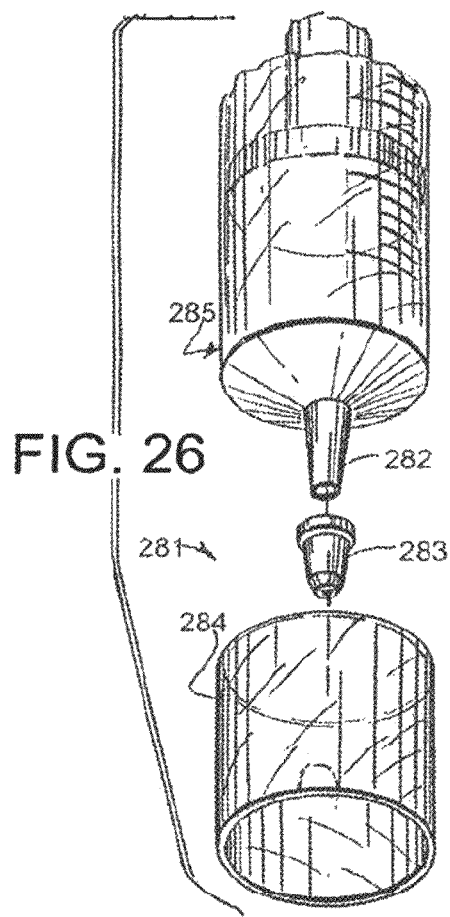
FIG. 26 is an exploded perspective view of yet another preferred embodiment of the splash shield of the present invention, showing a syringe-type end, a syringe adapter to control the irrigation stream, and a tubular splash shield element.
Figure 27:
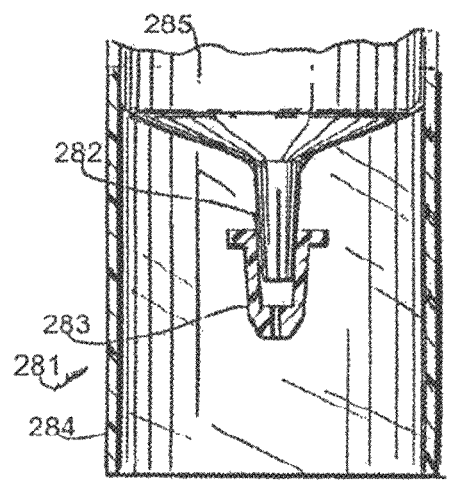
FIG. 27 is a sectional view of the embodiment of FIG. 26 illustrating the details with the parts connected.

FIG. 26 is an exploded perspective view of yet another preferred embodiment of the splash shield 281 of the present invention, showing a syringe-type tip 282, a syringe adapter 283 to control the irrigation stream, and a tubular splash shield component 284. FIG. 27 is a sectional view of the splash shield 281 of FIG. 26 illustrating the details with the parts connected. This arrangement provides a separate transparent shield component 284 which may be connected over a syringe body 285 to easily and quickly transform a standard syringe into a shield wound irrigation delivery device as shown in FIG. 27. One might want optionally to add adaptor 283 to the syringe tip 282 to modulate the flow. Providing a removable wound irrigation splash shield component 284 over the syringe body 285 would facilitate this by eliminating the need to reach into a potentially narrow, tight fitting sterile space to manipulate, position and exchange connectors.

Figure 28:
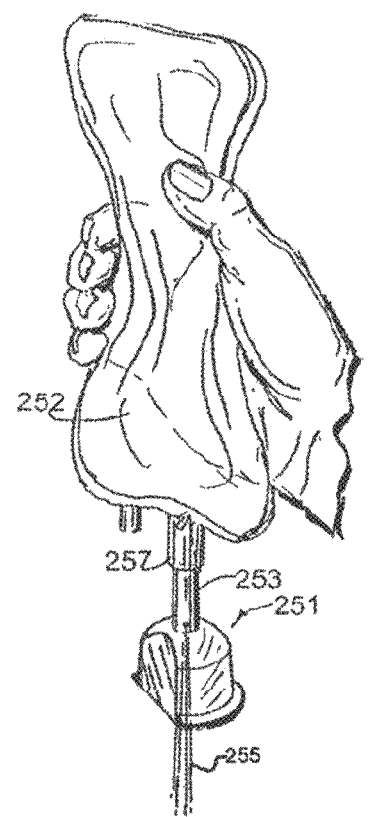
FIG. 28 is a perspective view of yet another preferred embodiment of a splash shield according to the present invention shown attached to an IV-type squeeze bag by way of the IV spike connector of this embodiment.
Figure 29:
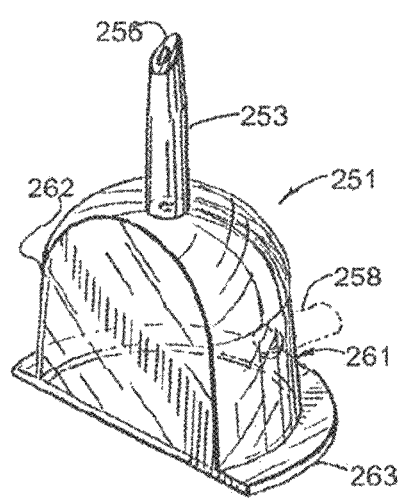
FIG. 29 is an enlarged (over FIG. 28) perspective view of the embodiment of FIG. 28.

FIG. 28 is a perspective view of yet another preferred embodiment of a splash shield 251 according to the present invention shown attached to an IV-type squeeze bag 252 by way of the IV spike connector 253 of splash shield 251. FIG. 29 is an enlarged (over FIG. 28) perspective view of the splash shield 251 of FIG. 28. FIG. 30 is sectional side view of the splash shield 251 of FIG. 28 illustrating the structural details thereof. FIG. 31 is a bottom view of the splash shield 251 of FIG. 28. Wound irrigation splash shield 251 is preferably transparent and engineered to be sterilizable and disposable as is commonly done in the medical industry. IV spike connector 253 (resembling a commonly available "IV spike") is a male connector with an inner conduit 254 for fluid 255 and a tapered pointed end 256 fits into the outlet end connector 257 of a fluid container such as a sterile IV solution bag 252 as shown in FIG. 28. Optionally, if desired, there might be an outlet 258 (dotted lines in FIG. 29) for the attachment to a vacuum source. In operation, fluid 255 is squeezed though conduit 254 of IV spike connector 253, from where it is forced through hole 259 of dividing surface 260 to form an irrigation stream through shield portion 261 (preferably shaped as shown, where, to better cover body wounds on appendages, as before mentioned, the preferred ratio of a maximum length of the open bottom end compared to a maximum width of such bottom end is at least 1.5:1.0) of wound irrigation splash shield 251. As shown, it is preferred that one (bottom) edge of the shield portion 261 be substantially linear so to provide a stable pivoting surface to promote a linearly directed irrigation stream. Also, one side 262 of shield portion 261 may preferably be substantially planar so as to increase the user's visibility of the irrigation process. Also, the irrigation stream may preferably be "off-center" to promote proximity to wall surfaces; that would allow better visualization. Also, it is preferred to provide a ledge 263 as shown at the bottom of shield portion 261 for better sealing against a skin portion when desired and for increasing the protective area of the device without increasing the width of the splash area required to form a seal.

FIG. 32 is a side elevation view of a preferred embodiment of the medical splash shield device 52 of the present invention. Preferably the device may be made of an inexpensive disposable transparent biocompatible medical grade plastic such as a US FDA class VI PVC or polycarbonate that may also be sterile to prevent wound infection. FIG. 33 is a top plan view of the splash shield device 52 of FIG. 32. FIG. 34 is a perspective view of the splash shield device 52 of FIG. 32 showing it in a restrained position, as on a portion of nearby equipment 19. FIG. 35 is a side sectional view of the splash shield device 52 of FIG. 32, illustrating its operation. As shown, the medical splash shield device 52 of this preferred embodiment includes proximal outlet 14 (embodying herein an output opening structured and arranged to allow suctioning excess irrigation fluid from within such body; wherein such output opening is structured and arranged to draw excess irrigation fluid from such splash portion toward a location approximately at a position symmetrically opposed (with respect to such maximum height dimension) from the location of such input opening), and a distal opening 17 for entry of the wound-washing fluid, shown as irrigation fluid 57. Preferably, distal opening 17 is located substantially lower than the maximum height dimension, as shown. The smooth rounded body 50 has an opening, as shown, which is either rectangular with rounded ends or a similar long oval in shape (seen most clearly in FIG. 33). Most of the illustrated bottom opening is portion 67 in a flat plane; but the distal end portion 51 of the bottom opening is in a plane coming upwards from the plane of portion 67 at about an angle of 30 degrees, as shown. A clip restraint 23 is preferably located near the top of the body 50 and protruding from the body 50 at about a parallel relationship to the protrusion of outlet 14. As shown, the proximal end wall 70 of body 50 is relatively vertical while the distal end wall 71 of body 50 rises very gradually at no more than about 45 degrees from the horizontal. The outlet 14 is located near the bottom-opening portion 67 and near the bottom of substantially vertical proximal end wall 70. The distal opening 17 preferably functions as an inlet and is located approximately centrally on the distal end wall 71.

Figure 36:
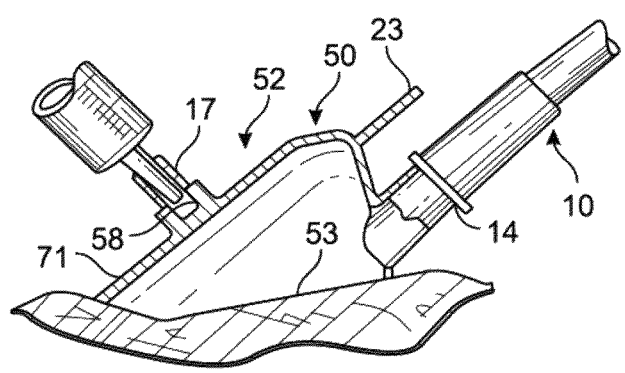
FIG. 36 is a side sectional view of the embodiment of FIG. 32, further illustrating operation with relief closure.

With reference to FIG. 35, the described preferred geometry permits the following operation (as shown) of splash shield device 52. The problems of prior art splash shield devices are overcome with the embodiment of FIGS. 32-36. The flushing irrigation fluid 57, as from syringe 55, irrigates wound 54 with a flow that flushes the debris toward and into vacuum line 10 by way of inlet end 12. Note that the placement of inlet end 12 near the flesh 53 portion of the splash shield device 52 assists in an efficient unidirectional flush flow to efficiently clean the wound 54 and remove debris and excess fluid (as shown). Preferably distal opening 17 is angled to assist in directing irrigation fluid at an oblique angle from vertical, so that a greater horizontal component of force from the fluid is imparted to flush debris out of the wound (embodying herein wherein such input opening is structured and arranged to assist in directing irrigation fluid at an oblique angle from vertical). Also, the elongated bottom shape (in an appropriate size) is more suited than a circular bottom shape for shielding and collecting flushing fluids on non-flat body parts such as arms, fingers, and feet. It is also noted that the relief afforded by the raised portion 51 of the shield bottom assists in providing more air flow (from an efficient direction) as needed for good flushing. And, as illustrated by FIG. 36 (a side sectional view of the embodiment of FIG. 32), the user may still press the splash shield device 52 toward the flesh 53 to operate the shield with relief closure as desired. This non-flat contour also assists in the pivoting of the device and the irrigation jet along the wound 54, changing the angle of the jet in relation to a position or location on the skin in a linear fashion.

Figure 37:
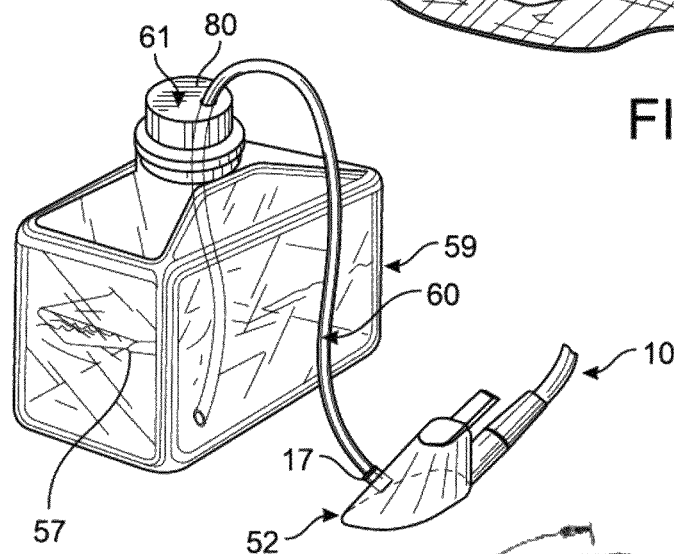
FIG. 37 is a perspective view of a preferred alternate usage of the splash shield of the type of FIG. 32, further illustrating siphoning of irrigation fluid from a fluid container.

FIG. 37 is a perspective view of a preferred alternate usage of the splash shield device 52 of the type of FIG. 32, further illustrating siphoning of irrigation fluid 57 from a fluid bottle 59 by way of tubing 60. Vent opening 61 is preferably provided in container cap 80 for well-known reasons.

Figure 38:
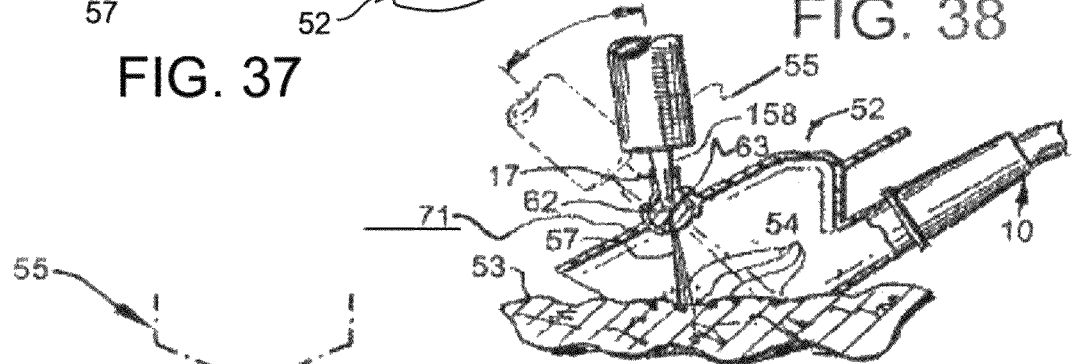
FIG. 38 is a side sectional view of an alternate preferred embodiment of the splash shield of the present invention, illustrating its operation incorporating an inlet swivel structure.
Figure 39:
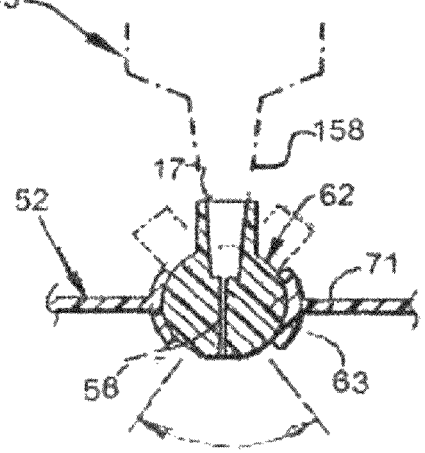
FIG. 39 is a partial expanded sectional view of the embodiment of FIG. 38, illustrating swivel detail.
Figure 40:
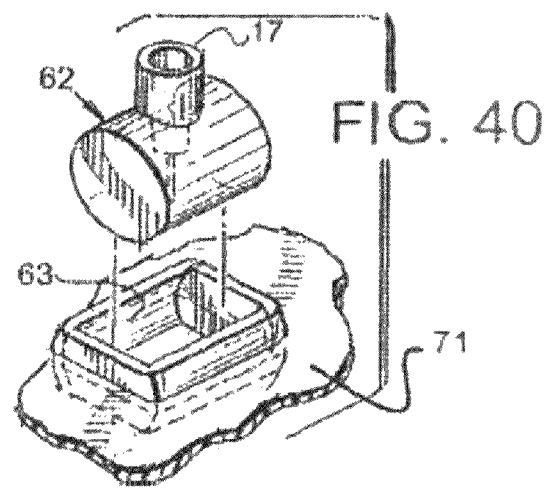
FIG. 40 is an exploded perspective view further illustrating the swivel detail of the embodiment of FIG. 38.

FIG. 38 is a side sectional view of an alternate preferred embodiment of the splash shield device 52 of the present invention, illustrating its operation incorporating an inlet swivel structure permitting better direction of impingement of the saline or other irrigation fluid 57, even for impinging along a wound length direction (as for wound 54) (embodying herein wherein such input opening comprises: a swivel structured and arranged to allow a user to direct a stream of irrigation fluid to selected portions of the skin of a patient; wherein such swivel comprises an attacher structured and arranged to allow attachment of a source of irrigation fluid to such swivel). The details of the inlet swivel structure are best shown in FIGS. 39-40. FIG. 39 is a partial expanded sectional view of the embodiment of FIG. 38, illustrating swivel detail. FIG. 40 is an exploded perspective view further illustrating the swivel detail of the embodiment of FIG. 38. As shown, inlet swivel 62 containing distal opening 17 rides and may rotate in swivel socket 63, which socket is fixed in place by fixed attachment with the distal end wall 71 of splash shield device 52. When the tip 158 of syringe 55 is inserted into distal opening 17, the orifice nozzle 58 of inlet swivel 62 is enabled (see FIG. 39) to direct fluid 56 into the splash shield as shown. The arrangements of FIGS. 32, 33, 34, 35, 36, 37, 38, 39, and 40 embody herein a body structured and arranged to contain irrigation fluid, wherein such body has a maximum height dimension, and an input opening structured and arranged to allow the irrigation fluid into such body, wherein such input opening is located at a substantially lower position than such maximum height dimension; and further embody herein wherein a bottom peripheral circumference of such body has an oval-like shape; and further embody herein wherein such body includes at least one bottom opening; wherein the ratio of a maximum length of such at least one bottom opening compared to a maximum width of such at least one bottom opening is at least 1.5:1.0.

FIG. 41 is a perspective view of yet another preferred embodiment of a splash shield 311 according to the present invention. Splash shield 311 is shown with an inlet port 312 attached to an irrigation syringe 313 and a vacuum connector port 314 attached to a vacuum line 315. FIG. 42 is a side view of the splash shield 311 of FIG. 41, shown attached to the irrigation syringe 313. FIG. 43 is a front view of the splash shield 311 of FIG. 41, with the irrigation syringe 313 in dotted lines. FIG. 44 is a side sectional view of the splash shield 311 of FIG. 41 showing the structural details and fluid flow directions. FIG. 45 is a top view of the splash shield 311 of FIG. 41. FIG. 46 is a partial sectional view through the section 46-46 of FIG. 42. FIG. 47 is a bottom view of the splash shield 311 of FIG. 41.

The illustrated preferred embodiment of splash shield 311 has multiple inlet ports 312 and 312*a*, with varying internal configurations so that various different kinds of syringes or other fluid containers may be attached and variations in spray fineness may be had. Inlet ports 312 and 312*a* have male and female connection potential to allow for multiple user preferences with a single manually-operated splash shield 311. Alternately to the inlet port configurations illustrated, such ports may in certain applications protrude into the splash shield 311 or be located within the wall of the splash shield 311. Vacuum connector port 314 is located adjacent base 318 of the splash shield 311 to assist in removal of fluid at the skin surface. As shown, a groove 319 at each bottom side of splash shield 311 acts as a conduit for allowing air and irrigation fluid and debris to be transported to vacuum connector port 314 when downward pressure against the skin is applied while there is a vacuum pull. The grooves 319 form an incomplete seal on a contact surface and widen the base of the splash shield 311, with the groove 319 against the skin becoming an aperture through which such contaminated fluid can be removed. Such groove(s) 319 are preferred to be located near the base of the splash shield 311 to prevent or minimize any visual obstruction caused by the vacuum apparatus features for an observer looking from above (embodying herein an output nozzle structured and arranged to attach to a vacuum line; a conduit structured and arranged to direct suction flow across such splash portion toward such output nozzle; wherein such conduit comprises at least one channel along a periphery of such body extending from such output nozzle to a location approximately at a position symmetrically opposed from the location of such input opening).

The inlet ports 312 and 312*a* are preferably made to extend in parallel fashion with the vacuum connector port 314 to simplify manufacturing tooling complexity and cost. It is noted that grooves 319 are preferably located adjacent the outer perimeter 321 of the splash shield 311, thus increasing the total surface area of the splash shield 311 without compromising the smaller area that can form an inner protective or operational seal against the skin for wound irrigation protection, particularly for areas of small surface area or sharp contour. For example, over the sharp edge of the chin, one could form an adequate seal with the inner perimeter formed by the inner wall of the groove(s)

319. The lateral outer edges of the grooves would increase the effective surface area protection beyond that formed within the inner seal. This device preferably has a longitudinally tapered base 318 or perimeter 321 to facilitate attachment over the skin; and it preferably has a relief port or contour 325 to facilitate the directional outflow of irrigation effluent or to allow the inflow of gas to facilitate the vacuum of irrigation fluid. It is noted that, if desired for certain uses, the vacuum connector port 314 may be eliminated; and the illustrated device can be operated with or without a vacuum source connected. It is noted that the inlet on the illustrated device is off center, thus providing a design that permits maximum pivoting ability while maintaining efficient shielding. It is also preferred to have flat side edges 318a and 318b of base 318 to maximize stability of the device when pivoted along the edge, as when one is irrigating along a linear laceration.

Figure 48:
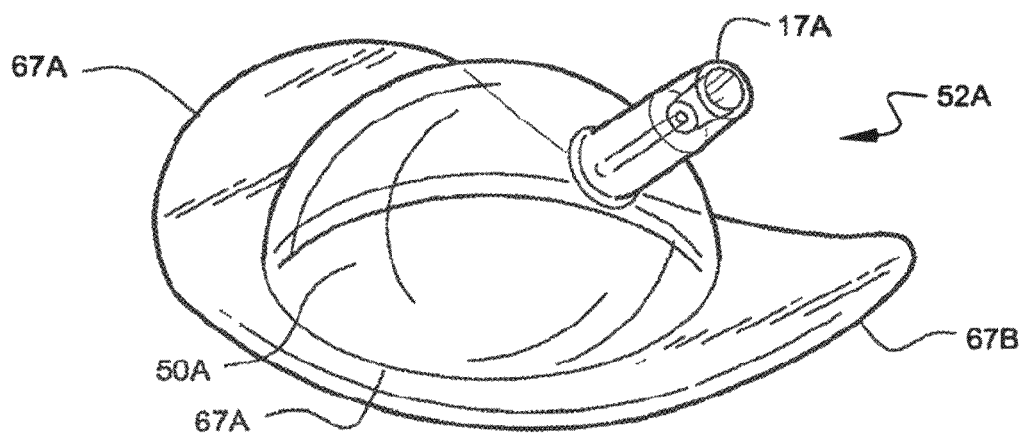
FIG. 48 is a perspective view of another preferred embodiment of a splash shield according to the present invention.
Figure 49:
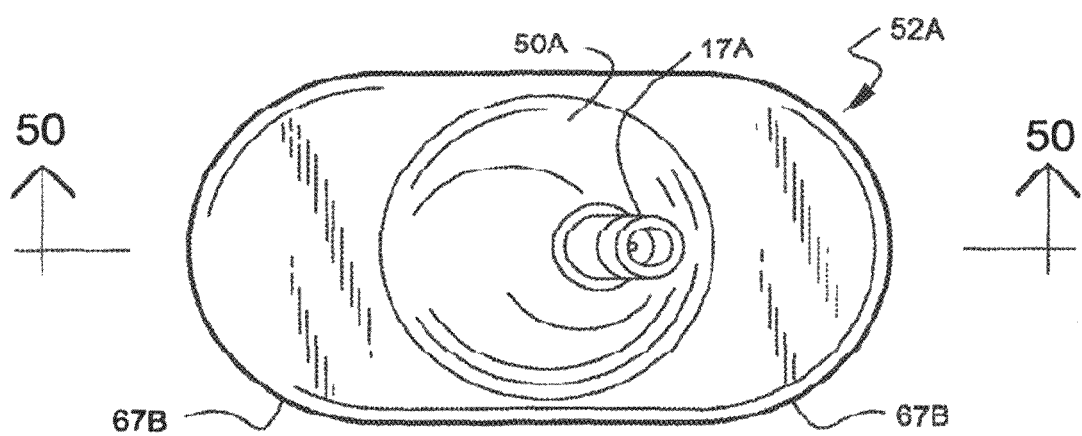
FIG. 49 is a top view of the embodiment of FIG. 48.
Figure 50:
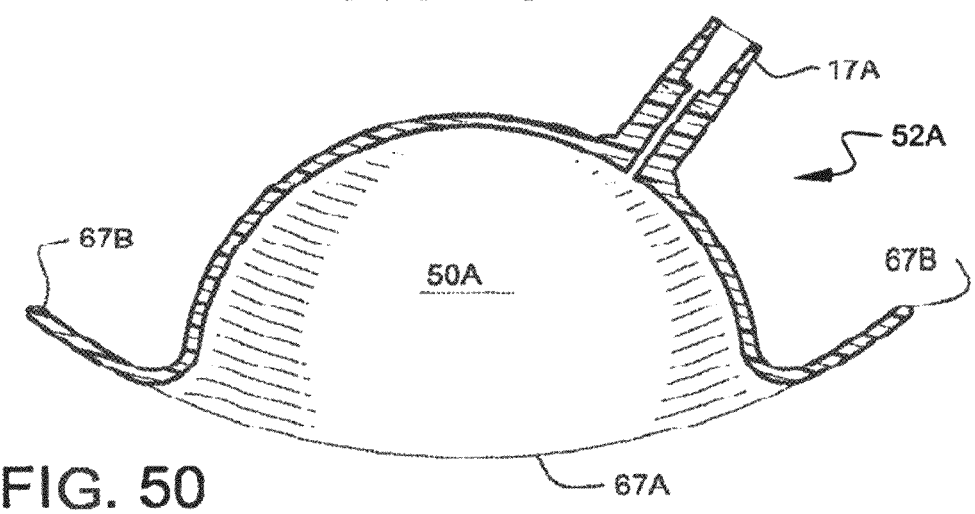
FIG. 50 is a sectional view through the section 50-50 of FIG. 49.

FIGS. 48 (a perspective view), 49 (a top view), and 50 (a sectional view through the section 50-50 of FIG. 49) illustrate another preferred embodiment of a splash shield 52A having many common advantages, arrangements and functions with splash shield device 52, with a few exceptions noted as follows. Bottom portion 67A preferably has a rounded periphery, preferably generally oval or circular, as shown. As shown, extending from this periphery is an extension 67B, as shown, with which to assist rocking of splash shield 52A to better direct the splash stream along the wound and also which performs a function of protecting the fingers and hands of the user from irrigation fluid and wound debris. As shown, bottom portion 67A also implements the "rocker" profile, having a non-planar bottom opening, and non-planar extension 67B. Preferably bottom portion 67A and extension 67B are "saddle-shaped", as shown (embodying herein a transparent body structured and arranged to assist in protecting a user from contact with irrigation fluid directed at a patient's wound; an irrigation-source connecter structured and arranged to connect such body, at a first end of such body, to a source of irrigation fluid; wherein such transparent body comprises at least one bottom opening wherein a bottom periphery of such at least one bottom opening is substantially non-planar; and further embodying herein wherein such bottom peripheral circumference is structured and arranged to allow rocking such body; and further embodying herein wherein such bottom peripheral circumference is saddle-shaped).

Figure 51:
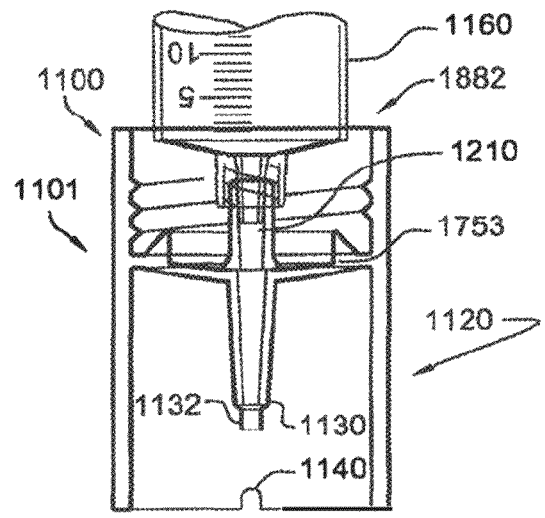
FIG. 51 shows a side view illustrating a wound irrigation system according to a preferred embodiment of the present invention.

FIG. 51 shows a side view illustrating a wound irrigation system according to a preferred embodiment of the present invention. Wound irrigation system 1100 preferably comprises wound irrigator 1101, as shown. Wound irrigator 1101 preferably shares many of the features of the aforementioned splash shields (see, e.g., splash shield 400). Preferably, wound irrigator 1101 connects to an irrigation fluid source and comprises shield 1120 and nozzle 1130, as shown. Wound irrigator 1101 is preferably connectable to different types of irrigation fluid sources at first end 1882, as shown. When an irrigation fluid source, such as bottle 1240 (see FIG. 53), is unconnected to wound irrigator 1101, second end 1882 is preferably open at second end 1882 to a hollow having a volume (such arrangement at least embodying herein at least one first irrigation source connector to connect such at least one body, at such at least one first end, to at least one squeezable wide mouth irrigation fluid bottle). Preferably, nozzle 1130 is surrounded by shield 1120 to advantageously prevent splashing of fluids onto a user of wound irrigator 1101, as shown. Nozzle 1130 preferably extends into hollow area of shield 1120, as shown (at least embodying herein wherein such at least one at least one irrigation fluid port projects into such at least one inner hollow). Shield 1120 is preferably open at its second end 1884, as shown. Nozzle 1130 preferably tapers as it approaches the open end of shield 1120, as shown. Wound irrigator 1101 also preferably comprises dividing structure 1753 situated between first end 1182 and second end 1884, as shown. Preferably, dividing structure 1753 is positioned closer to first end 1882 than to second end 1884, as shown. (Wound irrigator 1101 at least embodies herein an irrigation system comprising at least one body comprising at least one first end, at least one second end, and at least one inner hollow having at least one first volume wherein such at least one second end is open to such at least one inner hollow forming at least one shield).

In FIG. 51, wound irrigator 1101 is shown interconnected with syringe 1160. Wound irrigator 1101 preferably comprises syringe tip receiver 1210, as shown. Syringe tip receiver 1210 preferably comprises a projection, preferably tubular shaped, to receive a syringe tip. (Syringe tip receiver 1210 at least embodies herein at least one second irrigation source connector to connect such at least one body to at least one syringe, such at least one second irrigation source connector comprising at least one tubular member projecting in a direction toward such at least one first end).

In a preferred embodiment, syringe tip receiver 1210 preferably comprises a tapered interior portion (as shown) structured and arranged to make a luer-type connection with a luer-type syringe. In such a luer-type connection arrangement, a preferred inner diameter for syringe tip receiver 1210 would be about four millimeters, a preferred outer diameter for syringe tip projection 1210 would be about five millimeters, with a preferred height of about 10 millimeters. Further, in such a luer-type connection arrangement, syringe tip receiver 1210 preferably comprises a luer taper (preferably a six percent taper). Upon reading the teachings of this specification, those of ordinary skill in the art will now understand that, under appropriate circumstances, considering issues such as irrigation fluid source, size of the target to be irrigated, etc., other dimensions for syringe tip projection, such as, for example, outer diameters greater than five millimeters (e.g., six millimeter, 10 millimeters, etc.), outer diameters less than five millimeters (e.g., four millimeters, three millimeters, etc.), inner diameters greater than or less than four millimeters, heights greater than or less than 10 millimeters (e.g., 15 millimeters, 8 millimeters, 5 millimeters, 4 millimeters, etc.), etc., may suffice.

Syringe tip receiver 1210 preferably extends towards first end 1882, opposite the direction which nozzle 1130 extends, as shown. Preferably, syringe tip receiver 1210 is in fluid communication with nozzle 1130 so that irrigation fluid from syringe 1160 (or bottle 1240) may be delivered through nozzle 1130. (Nozzle 1130 at least embodies herein at least one irrigation fluid port to dispense fluid from such at least one squeezable wide mouth irrigation fluid bottle or such at least one syringe). As shown in FIGS. 2, 7, and 9, wound irrigator 1101 may also preferably comprise apertures in dividing structure 1753.

Wound irrigator 1101 may also preferably comprise stepped tip portion 1132, as shown. Stepped tip portion 1132 preferably permits attachment of tubing (see FIG. 10) (or a syringe; see FIG. 9). Used in this way, irrigation fluid will be dispensed from syringe tip receiver 1210. The walls surrounding syringe tip receiver 1210 will function as a shield in a manner similar to shield 1120. Additionally preferably, an irrigation fluid source may be connected to nozzle 1130 (see FIG. 9).

In a preferred embodiment, wound irrigator 1101 preferably has an overall height from first end 1882 to second end 1884 of about 60 millimeters. Wound irrigator 1101 is preferably cylindrical with a preferred outer diameter of about 40 millimeters and a preferred inner diameter of about 37 millimeters and a wall thickness of shield 1120 of about two millimeters. Shield 1120 (from dividing structure 1753 to second end 1884) preferably has a height of about 40 millimeters. The remaining portion of wound irrigator 1101 (from dividing structure 1753 to first end 1882) has a height of about 20 millimeters inches. Nozzle 1130 is preferably tapered, as shown. Nozzle 1130 preferably comprises a length of about 20 millimeters. Nozzle 1130 preferably comprises a diameter of from about 1 mm to about 3 mm, preferably about 1.5 mm, alternately preferably about 2 mm, alternately preferably about 2.5 mm. Upon reading the teachings of this specification, those skilled in the art will now appreciate that, under appropriate circumstances, considering such issues as cost, available materials, future technologies, etc., other dimensions, such as, for example, thicker or thinner walls, longer or shorter lengths, etc., may suffice.

Preferably, wound irrigator 1101 is a single monolithic piece.

In use, wound irrigator 1101 preferably irrigates a wound or an abscess (see, e.g., FIG. 54), preferably cleaning out infectious fluids to aid in healing. Fluid source (syringe 1160 or bottle 1240) pressurizes an irrigation fluid into wound irrigator 1101. Nozzle 1130 preferably directs irrigation fluid from the attached fluid source toward a wound or abscess. When irrigation fluid contacts the wound or abscess (or surrounding tissues), the irrigation fluid will deflect in multiple directions causing splashing of both the irrigation fluid and the body fluids being irrigated. Shield 1120 preferably blocks back-splash of fluids during irrigation, preferably minimizing the spread of such fluids. Upon reading the teachings of this specification, those of ordinary skill in the art will now understand that, under appropriate circumstances, wound irrigator may be used, for example, to clean debris from an ear.

To irrigate a wound using a syringe, syringe 1160 may be filled with irrigation fluid and then connected with syringe tip receiver 1210. Next, would irrigator is preferably positioned over the area to be irrigated or cleansed. Irrigation fluid within syringe 1160 may then be delivered to a wound or abscess by simply using the syringe. As previously noted, bottle 1240 may be used in irrigation.

Figure 52:
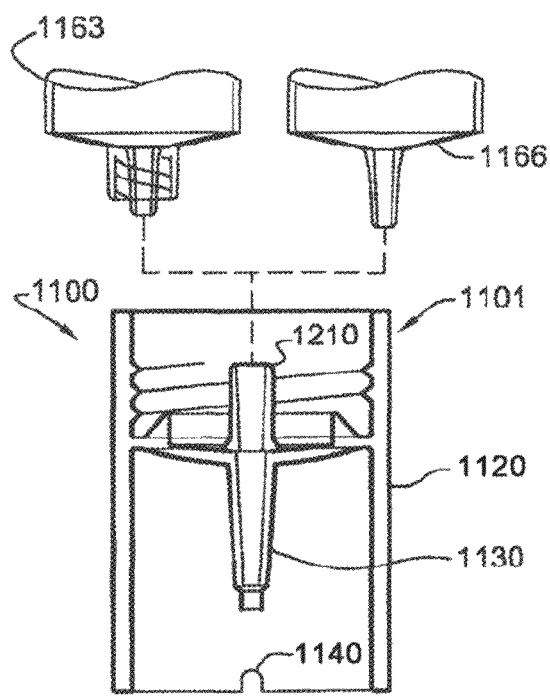
FIG. 52 shows a side view of the wound irrigation system of FIG. 51 illustrating multiple syringe-type connection.
Figure 53:
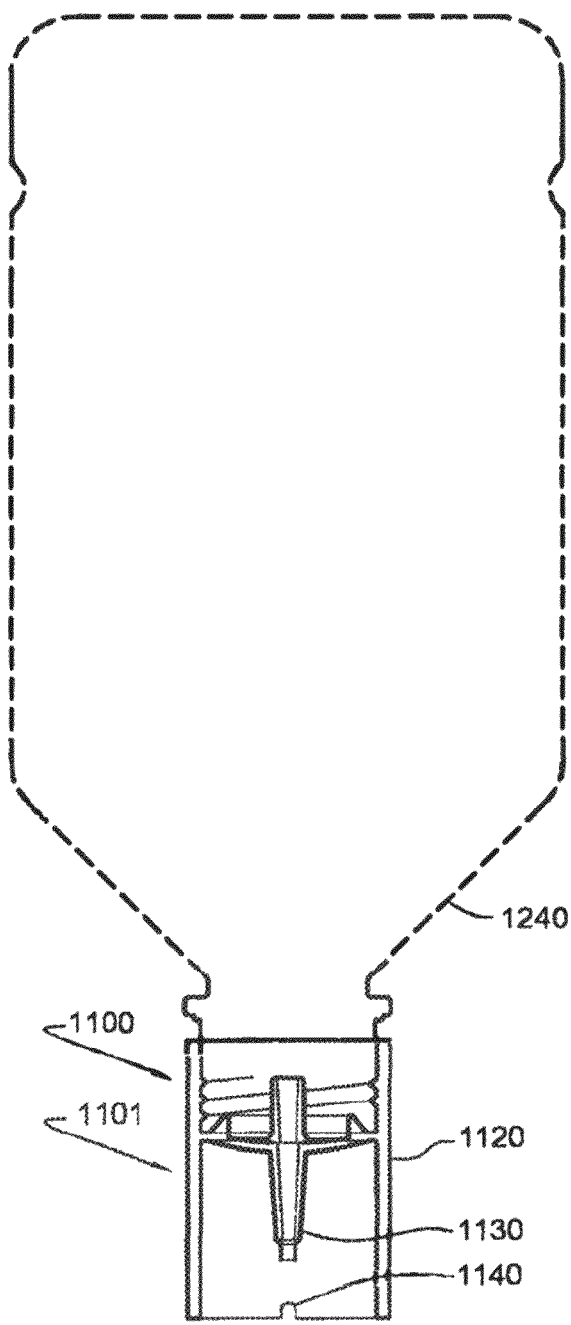
FIG. 53 shows a side view of the wound irrigation system of FIG. 51, illustrating attachment to an irrigation fluid bottle.

FIG. 52 shows a side view of the wound irrigation system of FIG. 51 illustrating multiple syringe-type connection. FIG. 53 shows a side view of the wound irrigation system of FIG. 51, illustrating attachment to an irrigation fluid bottle.

Syringe tip receiver 1210 of wound irrigator 1101 is preferably connectable to multiple types of syringes as shown in FIG. 52. Preferably, syringe tip receiver 1210 connects with such multiple types of syringes without leaking.

In one preferred embodiment, the interior of syringe tip receiver 1210 comprises a luer taper, preferably a female, six percent taper. As shown in FIG. 52, syringe tip receiver 1210 connects with syringe 1163 having a Luer-Lok connector and syringe 1166 having a Luer slip fit connector. Upon reading the teachings of this specification, those of ordinary skill in the art will now understand that, under appropriate circumstances, considering such issues as leakage prevention, then-available technology, etc., other types of syringe connectors to connect with syringe tip receiver may suffice, such as, for example, catheter tip syringes.

In addition to connection with various syringe types, wound irrigator 1101 is connectable with bottle 1240 as described more fully above (and as shown in FIG. 53). Depending on the wound to be irrigated or the irrigation fluid sources available, wound irrigator 1101 provides a convenient, single device which is connectable to a variety of irrigation fluid containers.

Wound irrigator 1101 preferably comprises plastic, preferably at least one inexpensive disposable transparent biocompatible medical grade plastic, preferably styrene or polycarbonate that is preferably sterilizable or preferably sterile. Wound irrigator 1101 preferably is clear/transparent, as shown, preferably for sighting of the irrigated area during irrigation. Upon reading the teachings of this specification, those skilled in the art will now appreciate that, under appropriate circumstances, considering such issues as cost, available materials, etc., other materials, such as, for example, Plexiglas, acrylics, nylons, other clear plastics, etc., may suffice.

Wound irrigator 1101 also may preferably comprise relief port 1140 to prevent undesired suction being applied to an irrigated wound or abscess, as shown. Relief port 1140 is preferably a "u-shaped" void in shield 1120 preferably located at the periphery of shield 1120, preferably at second end 1884, as shown. Wound irrigator 1101 preferably comprises at least one relief port 1140, as shown. In one preferred embodiment, wound irrigator 1101 comprises at least two of relief port 1140. When two of relief port 1140 are present in wound irrigator 1140, preferably the relief ports are positioned 90 degrees from one another. Upon reading the teachings of this specification, those of ordinary skill in the art will now understand that, under appropriate circumstances, considering such issues as shield diameter, size of target the target to be irrigated, etc., other numbers of relief ports and arrangements relative to other relief ports, etc., may suffice.

Relief port 1140 preferably allows pressure release from inside shield 1120 and preferably permits run-off of irrigation fluid. Upon reading the teachings of this specification, those skilled in the art will now appreciate that, under appropriate circumstances, considering such issues as cost, future technologies, etc., other relief ports, such as, for example, duck valves, high-on-wall breather ports, etc., may suffice.

Figure 54:
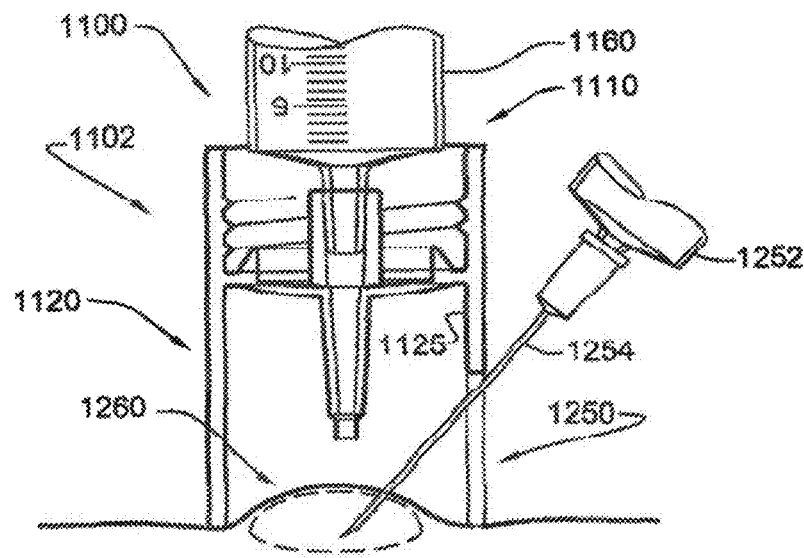
FIG. 54 shows a side view of a wound irrigation system, illustrating at least one syringe needle aperture, according to an alternately preferred embodiment of the present invention.
Figure 55:
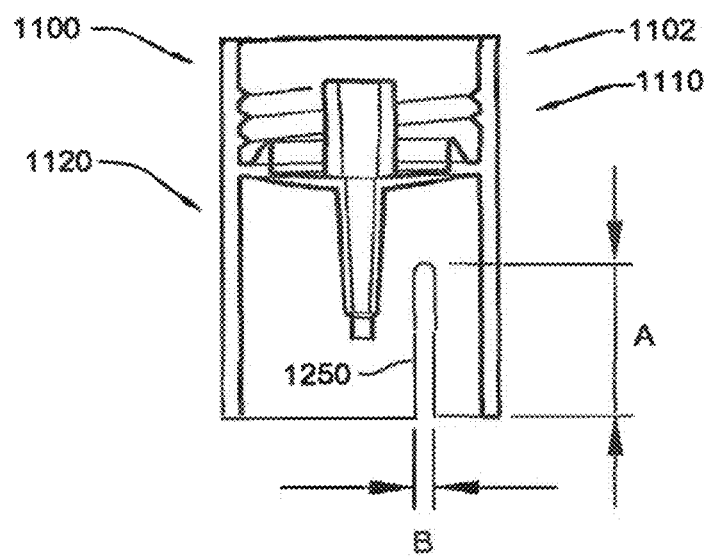
FIG. 55 shows a side view of the wound irrigation system of FIG. 54, illustrating syringe needle access.

FIG. 54 shows a side view of a wound irrigation system, illustrating at least one syringe needle aperture, according to an alternately preferred embodiment of the present invention. FIG. 55 shows a side view of the wound irrigation system of FIG. 54, illustrating syringe needleaccess.

Wound irrigation system 1100 alternately preferably comprises wound irrigator 1102, as shown. Wound irrigator 1102 is substantially similar to wound irrigator 1101. Wound irrigator 1102 comprises an elongated relief port or syringe needle aperture 1250. Syringe needle aperture 1250 is "taller" compared with relief port 1140 shown in FIG. 51. Syringe needle aperture 1250 preferably allows access to a wound (such as abscess 1260) with at least one syringe needle 1254, as shown in FIG. 54, preferably allowing syringe 1252 to be used in the treatment of abscess 1260. An abscess is a collection of pus that has accumulated in a cavity formed by the tissue typically in response to an infection. Abscess treatment typically involves incision and drainage. In the embodiment shown in FIGS. 54 and 55, a syringe needle may be manipulated to puncture the abscess, deliver additional irrigation fluid, etc. Upon reading the teachings of this specification, those skilled in the art will now appreciate that, under appropriate circumstances, considering such issues as future applications, cost, future technologies, etc., other instrument apertures, such as, for example, scalpel apertures, suction apertures, tweezers apertures, etc., may suffice.

Syringe needle aperture 1250 preferably comprises an opening in shield wall 1125, as shown. Syringe needle aperture 1250 preferably is wide enough for syringe needle 1254, and preferably tall enough to allow comfortable angling of syringe needle 1254 (and thereby syringe 1252) for use, as shown. Upon reading the teachings of this specification, those skilled in the art will now appreciate that, under appropriate circumstances, considering such issues as cost, future technologies, etc., other dimensions and aperture placements, such as, for example, circular apertures, angled apertures, wider apertures, t-slot apertures, membrane covered apertures, etc., may suffice.

Preferably, wound irrigator 1102 may be used as a splatter shield when injecting target tissue with a needle. Preferably wound irrigator 1102 is sterile so that any contact with a sterile needle.

Wounds and abscess are commonly injected with numbing medication. Frequently, the injected medication builds pressure up under the skin or in an abscess. With the built up pressure, the injected medication (including blood or pus) may erupt or burst, shooting blood and pus away from the area of injection which may make contact with a nearby person (and potentially come in contact with clothing or even an eye). Preferably, wound irrigator 1102 may be placed over an injection site (e.g., abscess 1260). Wound irrigator 1102 preferably being transparent permits a person to view the target area and grip wound irrigator while inserting syringe needle 1254 into needle aperture 1250 (see FIG. 54). When held in position, shield 1120 of wound irrigator 1102 preferably blocks the potential splatter of contents from the injected site. Further, wound irrigator 1102 advantageously prevents the needle handler from receiving inadvertent needle sticks as the syringe needle 1254 is virtually surrounded by splash shield 1120 when inserted into needle aperture 1250 (at least embodying herein wherein such at least one shield further comprises at least one void having a height substantially greater than its width and also at least embodying herein wherein such at least one shield further comprises at least one void sized to permit insertion and manipulation of a syringe needle). Preferably, wound irrigator 1102 is sterile so needle contact with the walls of needle aperture 1250 or wound irrigator 1102 will not contaminate the needle. Preferably, when in use, wound irrigator 1102 may be gripped securely from above. This method may also be performed with splash shield 400. Using splash shield 400, the shield is placed over a target area and a syringe needle is directed through the skin to the target. Upon reading the teachings of this specification, those of ordinary skill in the art will now understand that, under appropriate circumstances, considering issues such as device dimensions, intended use, etc., other splatter shield arrangements, such as cylindrical bodies with an open and a closed end with or without a syringe needle insertion aperture may suffice. The above description at least embodies herein a method relating to preventing spraying or splatter of fluid from an injection site comprising the steps of: placing at least one shield having at least one open end and at least one inner hollow over at least one portion of tissue to be injected; injecting such at least one portion of tissue to be injected; and shielding a user from any spraying or splattering resulting from the injection using such at least one shield. Additionally, the above description at least embodies herein such a method wherein such at least one shield comprises at least one aperture suitable to insert and manipulate at least one injecting device (e.g., a syringe).

FIG. 56 shows a side view of wound irrigation system 1100, illustrating nozzle extension 1300, according to an alternately preferred embodiment of the present invention. FIG. 57 shows a side view of wound irrigation system 1100 of FIG. 56, illustrating use of nozzle extension 1300. Wound irrigation system 1100 alternately preferably comprises abscess irrigator 1103, as shown. Abscess irrigator 1103 preferably comprises many of the elements of wound irrigator 1101, as shown. Abscess irrigator 1103 preferably further comprises nozzle extension 1300, as shown. Nozzle extension 1300 preferably comprises at least one nozzle connector 1310 and preferably at least one extended tip 1320, as shown. Nozzle connector 1310 preferably connects to irrigation nozzle 1130, preferably in a friction-fit, as shown. Extended tip 1320 preferably extends beyond splash shield 1120, as shown in FIG. 58. Preferably, nozzle extension 1300 preferably extends beyond shield 1120 a distance of about ¼ inch to about three inches. For most uses, nozzle extension 1300 preferably extends beyond shield 1120 a distance of about ½ inch. Upon reading the teachings of this specification, those of ordinary skill in the art will now understand that, under appropriate circumstances, considering issues such as depth of target irrigation source, size of irrigation fluid container, etc., other dimensions of nozzle extension extending beyond shield, such as, for example, greater than three inches, ⅛ inch, 5 inches, etc., may suffice.

In use, abscess irrigator 1103 is used to probe and irrigate at least one abscess cavity 1330, as shown in FIG. 57. Extended tip 1320 may preferably be used to enter abscess cavity 1330, as shown in FIG. 57, preferably directing irrigation fluids within abscess cavity 1330. Extended tip 1320 preferably is flexible, as shown in FIG. 57. Flexibility of extended tip 1320 preferably prevents further injury to surrounding tissues.

Figure 59:
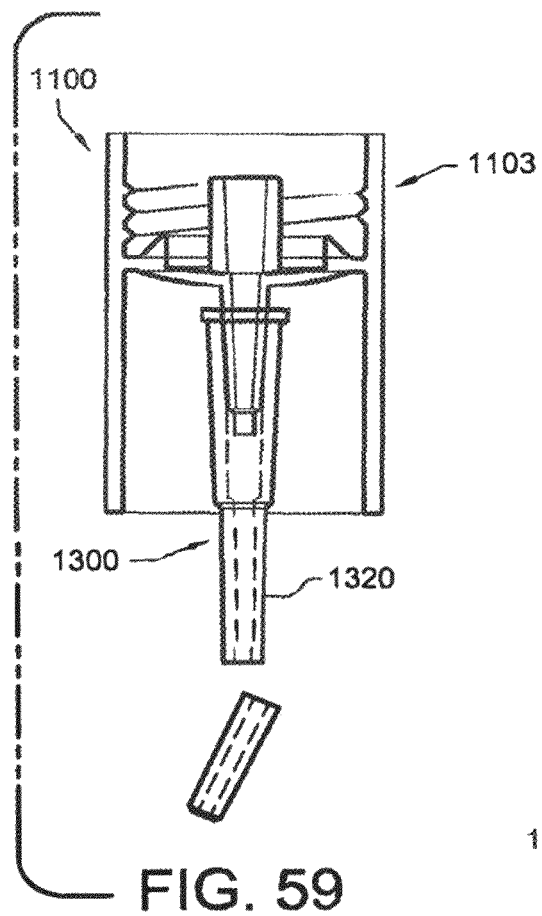
FIG. 59 shows a side view of the abscess irrigation system of FIG. 58, illustrating length adjustment of the nozzle extension.

FIG. 58 shows a side view of wound irrigation system 1100 of FIG. 56, illustrating attachment of nozzle extension 1300. FIG. 59 shows a side view of the abscess irrigation system of FIG. 58, illustrating length adjustment of the at least one nozzle extension. Nozzle extension 1300 preferably comprises plastic, preferably PVC plastic. Upon reading the teachings of this specification, those skilled in the art will now appreciate that, under appropriate circumstances, considering such issues as cost, available materials, etc., other materials, such as, for example, polyethylene, nylon, urethanes, polypropylene, etc., may suffice.

Nozzle extension 1300 (at least embodying herein at least one removable extension nozzle which, when attached to such at least one irrigation fluid port, extends beyond such at least one second end) preferably comprises at least one tapered tube, as shown. As shown in FIG. 59, extension tip 1320 preferably may be shortened, as shown, preferably by cutting, preferably to allow more versatility in use. Upon reading the teachings of this specification, those skilled in the art will now appreciate that, under appropriate circumstances, considering such issues as cost, available materials, etc., other nozzle extension geometries, such as, for example, cylindrical, stepped, etc., may suffice.

Figure 60:
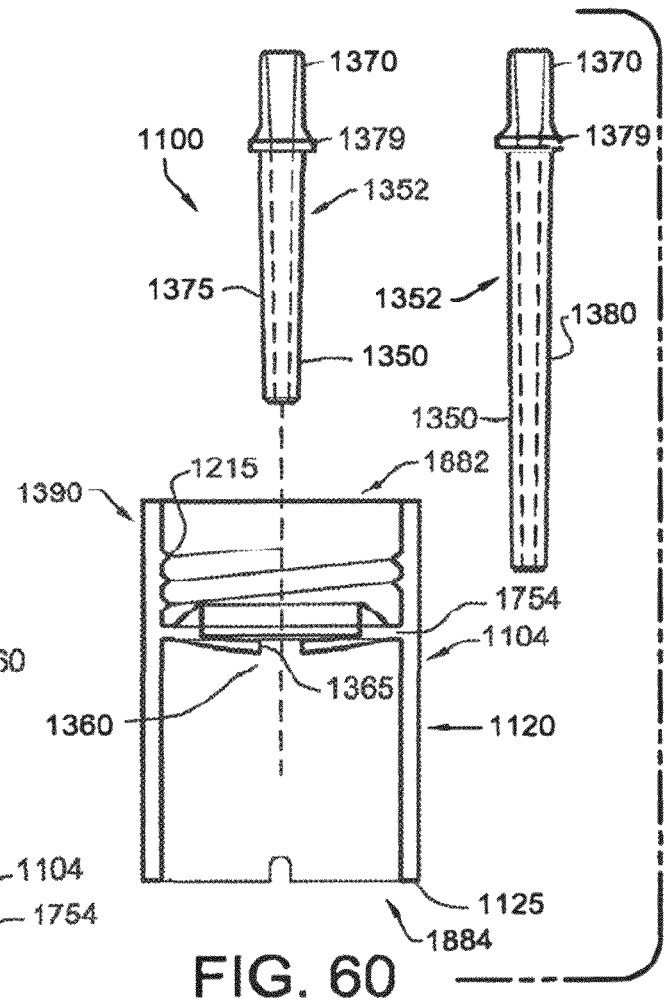
FIG. 60 shows a side view of an abscess irrigation system, illustrating an insert nozzle, according to an alternately preferred embodiment of the present invention.
Figure 61:
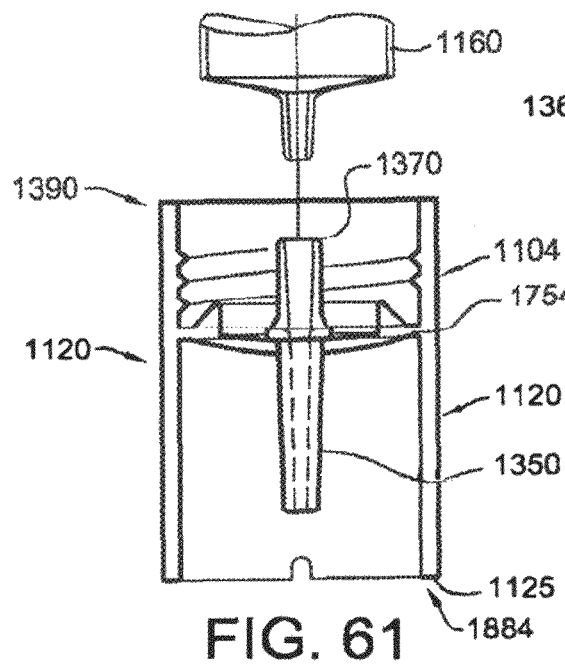
FIG. 61 shows a side view of the abscess irrigation system of FIG. 60, illustrating attachment of a syringe to the insert nozzle.

FIG. 60 shows a side view of abscess irrigation system, illustrating an insert nozzle (removable nozzle 1352), according to an alternately preferred embodiment of the present invention. FIG. 61 shows a side view of the abscess irrigation system of FIG. 60, illustrating attachment of at least one syringe to removable nozzle 1352. Wound irrigation system 1100 alternately preferably comprises abscess irrigator 1104, as shown. Abscess irrigator 1104 preferably comprises many of the elements of abscess irrigator 1101, as shown. However, instead of irrigation nozzle 1130, abscess irrigator 1104 preferably comprises removable nozzle 1352, as shown. Removable nozzle 1352 preferably comprises plastic, preferably PVC plastic. Upon reading the teachings of this specification, those skilled in the art will now appreciate that, under appropriate circumstances, considering such issues as cost, available materials, etc., other materials, such as, for example, polyethylene, nylon, urethanes, polypropylene, etc., may suffice.

Removable nozzle 1352 preferably comprises syringe tip receiver 1370 sized to receive a syringe without leaking. Preferably, syringe tip receiver 1370 may receive multiple types of syringe tips (see FIGS. 51 and 52 and related discussion). In one preferred embodiment, the interior of syringe tip receiver 1370 preferably comprises a luer taper, preferably a female, six percent taper. Preferably, syringe tip receiver 1370 interconnects with syringes having Luer-Lok connectors, Luer slip fit connectors, etc. Removable nozzle 1352 also preferably comprises at least one nozzle 1350, as shown. Abscess irrigator 1104 (at least embodying herein an irrigation system comprising: at least one body comprising at least one first end, at least one second end, and at least one inner hollow having at least one first volume wherein such at least one second end is open to such at least one inner hollow forming at least one shield) preferably comprises at least one nozzle aperture 1360 (an aperture in dividing structure 1753), as shown. Nozzle aperture 1360 is preferably present in dividing structure 1754 (at least embodying herein wherein such at least one dividing structure comprises at least one aperture) which separates second end 1884 from first end 1882 of wound irrigator 1104, as shown. Preferably, dividing structure 1754 is positioned closer to first end 1882 than to second end 1884, as shown (such arrangement at least embodying herein wherein such at least one dividing structure is positioned closer to such at least one second end than to such at least one first end). Removable nozzle 1352 (at least embodying herein at least one aperture-insertable member comprising at least one nozzle portion) preferably inserts into nozzle aperture 1360 up to a point where syringe tip receiver 1370 begins, as shown in FIG. 61. Removable nozzle 1352 preferably comprises larger-than-aperture portion 1379 (at least embodying herein at least one larger-than-aperture portion to secure such at least one aperture-insertable member in such at least one aperture) to secure removable nozzle 1352 in nozzle aperture 1360, as shown. Syringe tip receiver 1370 preferably connects with syringe 1160, as shown in FIG. 61 (see also FIG. 51). Removable nozzle 1352 preferably friction fits with aperture wall 1365, when inserted, as shown in FIG. 61. Upon reading the teachings of this specification, those skilled in the art will now appreciate that, under appropriate circumstances, considering such issues as cost, future technologies, etc., other removable nozzles, such as, for example, twist lock nozzles, two-piece nozzles, etc., may suffice.

Nozzle 1350 preferably comprises, as shown, at least one intra-shield nozzle 1375, alternately preferably at least one extra-shield nozzle 1380. Intra-shield nozzle 1375 preferably comprises a length shorter than splash shield 1120, as shown, preferably to keep nozzle 1350 inside shield wall 1125, when inserted, as shown in FIG. 61 (such arrangement at least embodying herein wherein, when such at least one aperture-insertable member is inserted into such at least one aperture, such at least one nozzle portion projects into such at least one inner hollow). Extra-shield nozzle 1380 (at least embodying herein wherein such at least one nozzle portion, when such at least one aperture-insertable member is inserted into such at least one aperture, extends beyond such at least one second end) preferably comprises a length longer than splash shield 1120, preferably protruding from splash shield 1120, when inserted.

FIG. 62 shows a side view of an irrigation system, illustrating at least one detachable shield, according to an alternately preferred embodiment of the present invention. Wound irrigation system 1100 alternately preferably comprises abscess irrigator 1105, as shown. While abscess irrigator 1105 comprises many elements of abscess irrigator 1101, instead of splash shield 1120 integral to abscess irrigator 1101, abscess irrigator 1105 preferably comprises removable splash shield 1420, as shown. Abscess irrigator 1105 preferably comprises at least one fluid source connector 1410 and at least one removable splash shield 1420, as shown.

While fluid source connector 1410 comprises many elements of fluid source connector 1110, fluid source connector 1410 preferably further comprises at least one shield connector 1430. Shield connector 1430 preferably allows attachment of removable splash shield 1420 to fluid source connector 1410, as shown. Removable splash shield 1420 preferably friction fits to fluid source connector 1410. Removable splash shield 1420 preferably comprises shield wall 1125, as shown. Removable splash shield 1420 preferably comprises at least one cylindrical tube. When removable splash shield 1420 is attached, irrigation nozzle 1130 preferably extends into removable splash shield 1420. Upon reading the teachings of this specification, those skilled in the art will now appreciate that, under appropriate circumstances, considering such issues as cost, future applications, etc., other removable splash shield geometries, such as, for example, conic, planar, concave, etc., may suffice.

FIG. 63 shows a side view of an irrigation system, illustrating at least one adjustable-height shield, according to an alternately preferred embodiment of the present invention. Wound irrigation system 1100 alternately preferably comprises abscess irrigator 1106, as shown. While abscess irrigator 1106 comprises many elements of abscess irrigator 1105, instead of shield connector 1430, abscess irrigator 1106 preferably comprises adjustable shield connector 1435, as shown. Adjustable shield connector 1435, via more surface area contact when compared with shield connector 1430 (at least embodying herein wherein such at least one shield connector is sized to permit position selection of such at least one shield) preferably allows removable shield 1420 to adjust in height. Removable shield 1420 preferably comprises at least one abbreviated shield 1424, alternately preferably at least one extended shield 1426, as shown. When using either abbreviated shield 1424 or extended shield 1426, irrigation nozzle 1130 preferably extends into each respective shield. Abbreviated shield 1424 preferably allows protrusion of irrigation nozzle 1130, when fully shortened on adjustable shield connector 1435. Extended shield 1426 preferably extends past irrigation nozzle 1130, when attached to adjustable shield connector 1435. Upon reading the teachings of this specification, those skilled in the art will now appreciate that, under appropriate circumstances, considering such issues as cost, future technologies, etc., other adjustable length splash shields, such as, for example, telescopic splash shields, flexible splash shields, etc., may suffice.

FIG. 64 shows a side view of an irrigation system, illustrating at least one multiple-type connector, according to an alternately preferred embodiment of the present invention. FIG. 65 shows a bottom view of the irrigation system of FIG. 64. FIG. 66 shows the sectional view 66-66 of FIG. 65. FIG. 67 shows a side view of the irrigation system of FIG. 66, illustrating attachment to at least one fluid bottle.

Wound irrigation system 1100 alternately preferably comprises irrigator 1107, as shown. Irrigator 1107 preferably comprises syringe connector 1510 and threaded connector 1525, as shown. Syringe connector 1510 preferably accepts connections, as shown in FIG. 64, from syringe 1160 (irrigation fluid sources 1165) preferably comprising, as shown, either slip-fit-type luer connector 1230, or alternately preferably comprising a luer-lock connector 1235. Upon reading the teachings of this specification, those of ordinary skill in the art will now understand that, under appropriate circumstances, considering such issues as the target of irrigation, irrigation fluid source container size, etc., other types of syringes may engage syringe connectors, such as, for example, catheter tip syringes, etc.

Additionally, threaded connector 1525 preferably allows connection to at least one fluid bottle 1240 (which may be wide mouth irrigation squeeze bottle 59), preferably comprising at least one threaded neck 1245, as shown in FIG. 67.

Further, irrigator 1107 preferably comprises at least one splash shield 1540, as shown in FIG. 65 and FIG. 66. Splash shield 1540 preferably functions similarly to splash shield 1120, preferably preventing back-splash of fluids during irrigation. Splash shield 1540 preferably comprises a concave dish, as shown. A preferred range for the depth of splash shield 1540 is about ½ inch to about 1½ inches. Upon reading the teachings of this specification, those of ordinary skill in the art will now understand that, under appropriate circumstances, considering issues such as desired ejecting pressure of fluid, area to be irrigated, size of irrigation fluid container, etc., other depths of splash shield, such as greater than 1½ inches (e.g., two inches, five inches, etc.) or less than ¼ inch (e.g., ⅛ inch, etc.), etc., may suffice.

Also upon reading the teachings of this specification, those skilled in the art will now appreciate that, under appropriate circumstances, considering such issues as cost, future technologies, etc., other splash shields, such as, for example, circular plates, extended concave dishes, etc., may suffice.

Irrigator 1107 preferably comprises nozzle 1530, as shown. Syringe connector 1510 is preferably in fluid communication with nozzle 1530 so that irrigation fluid from either a syringe attached at syringe connector 1510 or bottle 1240 (irrigation source 1165) will flow from the irrigation fluid source through nozzle 1530 to the intended target. Nozzle 1530 preferably extends beyond splash shield 1540, as shown. Such an extended nozzle is preferably used to irrigate abscesses (see, e.g., FIG. 57).

Figure 69:
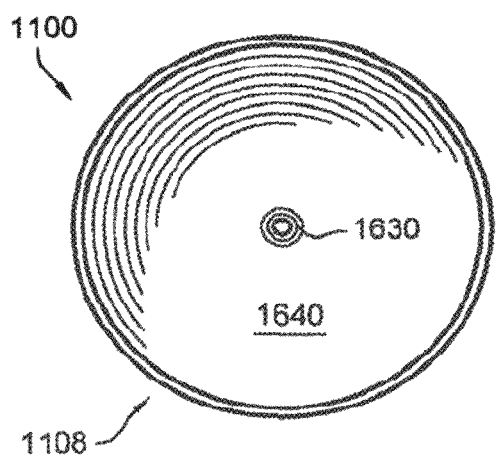
FIG. 69 shows a bottom view of the abscess irrigation system of FIG. 68.
Figure 68:
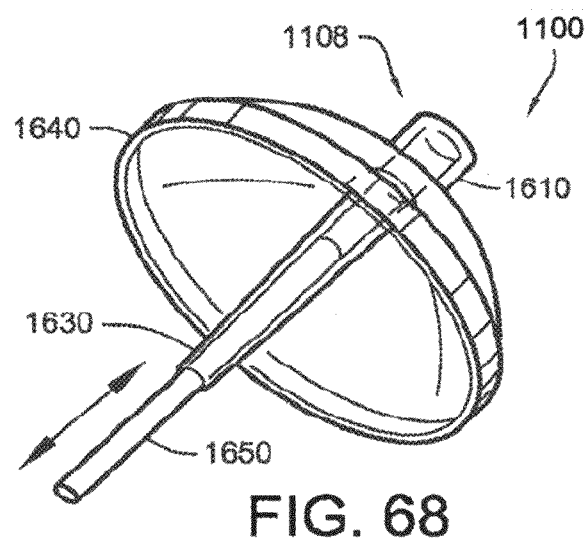
FIG. 68 shows a perspective view of an abscess irrigator according to an alternately preferred embodiment of the present invention.

FIG. 68 shows a perspective view of an abscess irrigator (abscess irrigator 1108) according to an alternately preferred embodiment of the present invention. FIG. 69 shows a bottom view of the abscess irrigation system of FIG. 68. Wound irrigation system 1100 alternately preferably comprises at least one abscess irrigator 1108, as shown. Abscess irrigator 1108 preferably comprises at least one syringe connector 1610, at least one irrigation nozzle 1630, and at least one splash shield 1640, as shown. Splash shield 1640 preferably comprises at least one thickened wall portion at the rim of the open end of splash shield 1640, as shown. Such thickened wall portion preferably assists in gripping and handling abscess irrigator 1108.

Preferably syringe connector 1610 is structured and arranged to be in fluid communication with irrigation nozzle 1630 so that fluid from an irrigation fluid source (e.g., a syringe) connected at syringe connector 1610 may flow through irrigation nozzle 1630 and be delivered at the desired target. In another preferred embodiment, tubing may be preferably connected with syringe connector 1610 (see, e.g., FIG. 11).

Splash shield 1640 preferably comprises at least one concave dish structure or a dome-shaped configuration open at one end, as shown, preferably comprising a diameter of about 40 millimeters, and preferably comprising a depth of about 1½ centimeters. Splash shield 1640 preferably comprises at least one inner surface and at least one outer surface. A preferred range for the depth of splash shield 1640 is about ½ inch to about 1½ inches. Upon reading the teachings of this specification, those of ordinary skill in the art will now understand that, under appropriate circumstances, considering issues such as irrigation target, irrigation source size, amount of fluid desired to be delivered, etc. diameters of splash shield other than 40 millimeters (such as 50 millimeters, greater than 50 millimeters, 45 millimeters, less than 45 millimeters, etc.) and depths other than 1½ centimeters (such as 30 millimeters, greater than 15 millimeters, 1 centimeter, four centimeters, five centimeters, etc.), may suffice. Also, upon reading the teachings of this specification, those of ordinary skill in the art will now understand that, under appropriate circumstances, considering such issues as irrigation target, irrigation source size, amount of fluid desired to be delivered, material used, cost, etc., other splash shield shapes, such as, for example, shallower cylindrical dish shields, planer shields, conical shields, etc., may suffice.

Splash shield 1640 preferably is transparent, as shown. The transparency permits a user to view the target being irrigated through the device. Splash shield 1640 preferably comprises plastic, preferably at least one inexpensive disposable transparent biocompatible medical grade plastic, preferably a styrene or polycarbonate that may also be sterile to prevent wound infection. Upon reading the teachings of this specification, those skilled in the art will now appreciate that, under appropriate circumstances, considering such issues as available materials, cost, etc., other materials, such as, for example, Plexiglas, acrylics, nylons, other clear plastics, etc., may suffice.

Figure 70:
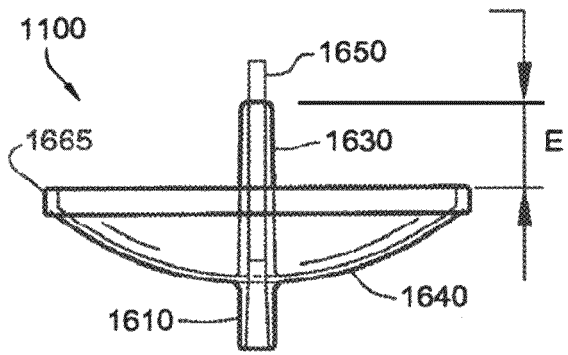
FIG. 70 shows a side view of the abscess irrigation system of FIG. 68.

FIG. 70 shows a side view of the abscess irrigation system of FIG. 68. Irrigation nozzle 1630 preferably is surrounded by and extends beyond splash shield 1640, as shown, preferably a distance E, preferably about 1½ centimeters (such arrangement at least embodying herein such at least one shield surrounding such at least one fluid output port and wherein such at least one fluid output port extends beyond such at least one open end of such at least one shield). Upon reading the teachings of this specification, those of ordinary skill in the art will now understand that, under appropriate circumstances, considering issues such as target to be irrigate, size of the connected irrigation source, etc., irrigation nozzle may extend beyond splash shield other lengths, such as, for example, 18 millimeters, 30 millimeters, one inch, greater than 30 millimeters, greater than one inch, etc.

Irrigation nozzle 1630 preferably comprises rigid plastic, preferably at least one inexpensive disposable transparent biocompatible medical grade plastic, preferably a styrene or polycarbonate that may also be sterile to prevent wound infection. Upon reading the teachings of this specification, those skilled in the art will now appreciate that, under appropriate circumstances, considering such issues as cost, available materials, etc., other materials, such as, for example, polyethylene, nylon, urethanes, polypropylene, etc., may suffice.

Figure 71:
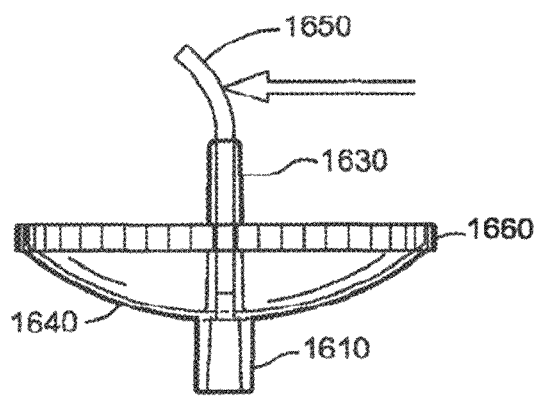
FIG. 71 shows a side view of the abscess irrigation system of FIG. 70, illustrating at least one flexible nozzle extension.

FIG. 71 shows a side view of the abscess irrigation system of FIG. 70, illustrating flexible nozzle extension 1650. In a preferred embodiment, irrigation nozzle 1630 preferably comprises flexible nozzle extension 1650, as shown. (It is noted that in another preferred embodiment flexible nozzle extension 1650 is preferably not included in abscess irrigator 1108.) Flexible nozzle extension 1650 preferably slides in and out of irrigation nozzle 1630 adjusting the effective length of irrigation nozzle 1630, as shown, during use. Flexible nozzle extension 1650 is preferably held in position within irrigation nozzle 1630 with a friction fit. The aforementioned friction fit holds flexible nozzle extension 1650 in position within irrigation nozzle 1630. Flexible nozzle extension 1650 preferably comprises flexible plastic, preferably PVC plastic.

Figure 72:
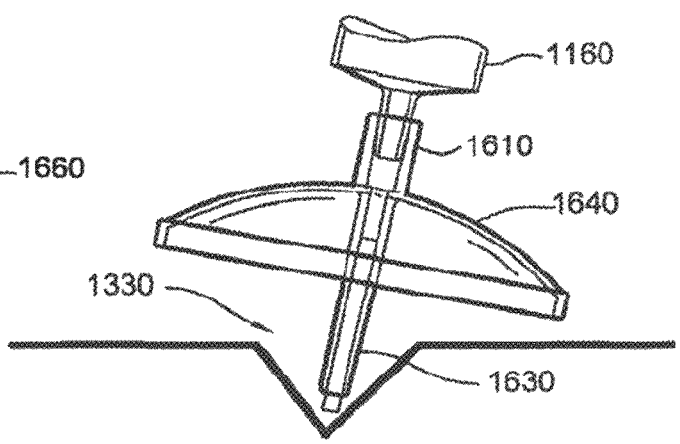
FIG. 72 shows a side view of the abscess irrigation system of FIG. 71, illustrating use with at least one abscess cavity.

FIG. 72 shows a side view of the abscess irrigation system of FIG. 71, illustrating use with abscess cavity 1330. Syringe connector 1610 preferably allows attachment to syringe 1160, as shown, to be used as an irrigation fluid source. In use, irrigation nozzle 1630 preferably may be inserted into abscess cavity 1330, as shown, to clean abscess cavity 1330 of infectious fluids. Splash shield 1640 preferably prevents excessive back-splash of irrigation fluids and infectious fluids, while allowing sighting of abscess area. For additional length in probing and irrigating abscess, flexible nozzle extension 1650 may be extended from irrigation nozzle 1630 (see, e.g., FIG. 68). A flexible extension nozzle is preferred so that trauma will not be increased when irrigating an abscess (which typically needs to be incised to let the abscess contents drain).

Figure 73:
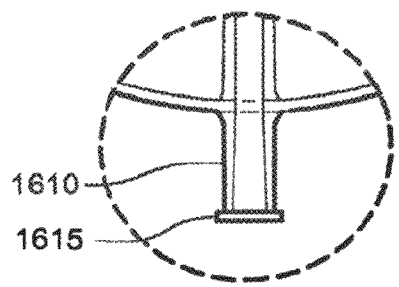
FIG. 73 shows a side view, illustrating an alternately preferred luer-lock attacher, according to an alternately preferred embodiment of the present invention.

FIG. 73 shows a side view, illustrating an alternately preferred luer-lock connector, according to the preferred embodiment of FIG. 72. Syringe connector 1610 alternately preferably further comprises at least one locking ridge 1615, as shown. Locking ridge 1615 preferably engages with twist-lock-type luer-locking connectors, such as is shown in syringe 1163 of FIG. 52, preferably to lock connection with syringe connector 1610. Upon reading the teachings of this specification, those skilled in the art will now appreciate that, under appropriate circumstances, considering such issues as cost, available fluid sources, etc., other locking mechanisms, such as, for example, bayonet locks, snap locks, etc., may suffice.

Upon reading the teachings of this specification, those of ordinary skill in the art will now understand that, under appropriate circumstances, considering such issues as intended target, size of intended target, type of stream to be directed at target, other uses of abscess irrigator, such as, use to irrigate an ear to remove debris from an ear, use with a wound, etc., may suffice.

Although applicant has described applicant's preferred embodiments of this invention, it will be understood that the broadest scope of this invention includes modifications such as diverse shapes, sizes, and materials. Such scope is limited only by the below claims as read in connection with the above specification. Further, many other advantages of applicant's invention will be apparent to those skilled in the art from the above descriptions and the below claims.

What is claimed is:

1. A fluid delivery system for delivering a volume of fluid from a fluid source to a body surface or opening, the system comprising:
    a fluid source connector;
    a shield connector;
    a fluid delivery nozzle extending beyond the shield connector; and
    an extended shield configured to be removably attached to the shield connector such that a distal tip of the fluid delivery nozzle does not extend beyond a distal end of the extended shield;
    wherein the shield connector forms an inner hollow around at least a proximal portion of the fluid delivery nozzle.

2. The system of claim 1, wherein the shield connector is an adjustable shield connector configured to allow an axial position of the extended shield to be adjusted while the extended shield is attached to the adjustable shield connector.

3. The system of claim 2, wherein the adjustable shield connector is a circumferential wall that completely encircles at least a proximal portion of the fluid delivery nozzle along a longitudinal axis of the fluid delivery nozzle.

4. The system of claim 1, wherein the fluid delivery nozzle extends beyond the shield connector a distance in a range from about 15 millimeters to about 30 millimeters.

5. The system of claim 1, wherein the fluid delivery nozzle extends beyond the shield connector a distance of about 15 millimeters or about 18 millimeters.

6. The system of claim 1, wherein the shield connector circumferentially surrounds a proximal portion of the fluid delivery nozzle.

7. A method for delivering a volume of fluid from a fluid source to a body surface or opening using the system of claim 1, the method comprising:
    removably connecting the fluid source connector to the fluid source;
    directing the volume of fluid from the fluid source to the fluid delivery nozzle; and
    dispensing the volume of fluid from the fluid delivery nozzle to the body surface or opening.

8. The method of claim 7, wherein the distal tip of the fluid delivery nozzle penetrates the body surface or opening during the dispensing step.

9. The method of claim 7, wherein the distal tip of the fluid delivery nozzle does not penetrate the body surface or opening during the dispensing step.

10. A fluid delivery system for delivering a volume of fluid from a fluid source to a body surface or opening comprising:
    a body comprising:
        a fluid source connector;
        a fluid delivery nozzle comprising a longitudinal axis and a distal tip; and
        a shield forming an inner hollow and comprising a circumferential wall that completely encircles at least a proximal portion of the fluid delivery nozzle along the longitudinal axis,
        wherein the distal tip of the fluid delivery nozzle is distal to a distal end of the circumferential wall.

11. The system of claim 10, wherein when the fluid source connector is connected to an irrigation fluid source, the distal tip of the fluid delivery nozzle is pointed away from the irrigation fluid source and the fluid source connector.

12. The system of claim 10, wherein the body is monolithic.

13. The system of claim 10, further comprising an extended shield configured to be removably attached to the body such that the fluid delivery nozzle does not extend beyond a distal end of the extended shield.

14. The system of claim 13, wherein the extended shield is configured to be removably attached to the circumferential wall.

15. The system of claim 13, wherein the distal tip of the fluid delivery nozzle is completely surrounded along the longitudinal axis by the extended shield.

16. The system of claim 13, wherein the distal tip of the fluid delivery nozzle is partially surrounded along the longitudinal axis by the extended shield.

17. The system of claim 10, wherein the circumferential wall is transparent.

18. The system of claim 17, wherein the distal tip of the fluid delivery nozzle extends beyond the distal end of the circumferential wall a distance of about 30 millimeters or less.

19. The system of claim 17, wherein the distal tip of the fluid delivery nozzle extends beyond the distal end of the circumferential wall a distance of about 15 millimeters or about 18 millimeters.

20. A method for delivering a volume of fluid from a fluid source to an abscess or wound, the method comprising:
  (i) connecting a fluid source to an irrigation device capable of adopting an abscess irrigation configuration and a wound irrigation configuration, the irrigation device comprising:
    a body comprising an irrigation source connector, a shield connector, and a fluid delivery nozzle; and
    a removable shield configured to be removably attached to the shield connector;
  wherein the fluid delivery nozzle comprises a distal tip configured to dispense the volume of fluid to the abscess or wound;
  wherein the distal tip is positioned distal to a distal end of the shield connector and proximal to a distal end of the removable shield when the shield is removably attached to the body; and
either or both of steps (ii) and (iii):
  wherein step (ii) comprises:
    (a) providing the irrigation device in the wound irrigation configuration wherein the removable shield is attached to the shield connector;
    (b) securing the irrigation device against a skin surface, such that the distal tip of the fluid delivery nozzle does not protrude below the skin surface; and
    (c) dispensing the volume of fluid from the fluid delivery nozzle; and
  wherein step (iii) comprises:
    (a) providing the irrigation device in the abscess irrigation configuration, wherein the removable shield is not attached to the shield connector;
    (b) inserting the irrigation device below the skin surface such that the distal tip of the fluid delivery nozzle protrudes below the skin surface; and
    (c) dispensing the volume of fluid from the fluid delivery nozzle below the skin surface.

* * * * *